US012144800B2

(12) United States Patent
Abel-Santos et al.

(10) Patent No.: US 12,144,800 B2
(45) **Date of Patent: *Nov. 19, 2024**

(54) INHIBITING GERMINATION OF CLOSTRIDIUM PERFRINGENS SPORES TO REDUCE NECROTIC ENTERITIS

(71) Applicant: The Board of Regents of the Nevada System of Higher Education on Behalf of the University of Nevada, Las Vegas, Las Vegas, NV (US)

(72) Inventors: Ernesto Abel-Santos, Las Vegas, NV (US); Norma Ramirez, Guanajuato (MX); Marc Liggins, Irvine, CA (US)

(73) Assignee: THE BOARD OF REGENTS OF THE NEVADA SYSTEM OF HIGHER EDUCATION ON BEHALF OF THE UNIVERSITY OF NEVADA, LAS VEGAS, Las Vegas, NV (US)

( * ) Notice: Subject to any disclaimer, the term of this patent is extended or adjusted under 35 U.S.C. 154(b) by 138 days.

This patent is subject to a terminal disclaimer.

(21) Appl. No.: 17/168,155

(22) Filed: Feb. 4, 2021

(65) Prior Publication Data

US 2021/0228550 A1 Jul. 29, 2021

Related U.S. Application Data

(63) Continuation of application No. 16/236,919, filed on Dec. 31, 2018, now Pat. No. 10,945,996, which is a continuation of application No. 15/545,645, filed as application No. PCT/US2016/016848 on Feb. 5, 2016, now abandoned.

(60) Provisional application No. 62/113,184, filed on Feb. 6, 2015.

(51) Int. Cl.

| | |
|---|---|
| ***A61K 31/428*** | (2006.01) |
| ***A23K 20/195*** | (2016.01) |
| ***A61K 9/00*** | (2006.01) |
| ***A61K 9/14*** | (2006.01) |
| ***A61K 45/06*** | (2006.01) |
| *A61K 9/16* | (2006.01) |

(52) U.S. Cl.

CPC .......... *A61K 31/428* (2013.01); *A23K 20/195* (2016.05); *A61K 9/0056* (2013.01); *A61K 9/14* (2013.01); *A61K 45/06* (2013.01); *A61K 9/1611* (2013.01)

(58) Field of Classification Search

None

See application file for complete search history.

(56) References Cited

U.S. PATENT DOCUMENTS

| | | | | |
|---|---|---|---|---|
| 4,088,770 | A * | 5/1978 | Paget, Jr. | C07D 263/58 504/270 |
| 5,824,698 | A | 10/1998 | Hasler et al. | |
| 6,326,364 | B1 | 12/2001 | Lin et al. | |
| 8,124,623 | B2 | 2/2012 | Hubschwerlen et al. | |
| 8,389,516 | B2 | 3/2013 | Haydon et al. | |
| 8,618,100 | B2 | 12/2013 | Guillemont et al. | |
| 9,079,935 | B2 | 7/2015 | Abel-Santos et al. | |
| 9,862,744 | B2 | 1/2018 | Abel-Santos et al. | |
| 10,945,996 | B2 * | 3/2021 | Abel-Santos | A61K 9/0056 |
| 2007/0112048 | A1 | 5/2007 | Bavari et al. | |
| 2008/0254010 | A1 | 10/2008 | Sasser et al. | |
| 2010/0168203 | A1 | 7/2010 | Levin et al. | |
| 2011/0086797 | A1 | 4/2011 | Dworkin | |
| 2011/0183360 | A1 | 7/2011 | Rajagopal et al. | |
| 2011/0229583 | A1 | 9/2011 | Tran et al. | |
| 2011/0280847 | A1 | 11/2011 | Sorg et al. | |
| 2012/0020950 | A1 | 1/2012 | Davis et al. | |
| 2014/0045808 | A1 | 2/2014 | Abel-Santos | |
| 2016/0175223 | A1 | 6/2016 | Dayan | |
| 2018/0000793 | A1 | 1/2018 | Abel-Santos | |
| 2018/0311259 | A1 | 11/2018 | Stappenbeck et al. | |
| 2023/0174505 | A1 | 6/2023 | Farber | |

FOREIGN PATENT DOCUMENTS

| | | | | |
|---|---|---|---|---|
| CS | 275631 * | | 3/1992 | C07D 277/74 |
| WO | WO-2002/060879 | A2 | 8/2002 | |
| WO | WO-2003/105846 | A1 | 12/2003 | |
| WO | WO-2004/041209 | A2 | 5/2004 | |
| WO | WO-2006/076009 | A2 | 7/2006 | |
| WO | WO-2007/056330 | A1 | 5/2007 | |
| WO | WO-2007/148093 | A1 | 12/2007 | |
| WO | WO-2010/062369 | A2 | 6/2010 | |
| WO | WO-2016/127102 | A2 | 8/2016 | |

OTHER PUBLICATIONS

Sidoova et al., CAS SciFinder (Database CAPLUS AN:1994:270377) English language abstract of CS275631 (1992).*

Abel-Santos, E. et al., 2007. Differential nucleoside recognition during Bacillus cereus 569 (ATCC I0876) spore germination. New J. Chem. 31 (5):748-755.).

Archimandritis, et al., Clostridium difficile colitis associated with a 'triple' regimen, containing clarithromycin and metronidazole, to eradicate Helicobacter pylori, J. Int. Med., 1998, 243(3), 251-253.

Bandyopadhyay, P., et al., 2001. Ion conductors derived from cholic acid and spermine: Importance of facial hydrophilicity on Na+ transport and membrane selectivity. J. Am. Chem. Soc. 123(31):7691-7696.

Bertolini et al., A New Rational Hypothesis for the Pharmacophore of the Active Metabolite of Leflunomide, a Potent Immunosuppressive Drug, J. Med. Chem., 1997, 40, 2011-2016.

(Continued)

*Primary Examiner* — Brian J Davis

(74) *Attorney, Agent, or Firm* — Ballard Spahr LLP

(57) ABSTRACT

Provided herein are materials and methods useful for reducing, preventing, and/or inhibiting germination of *C. perfringens* spores, including methods for inhibiting *C. perfringens* germination to reduce necrotizing enteritis (NE, also referred to as necrotic enteritis) in animals. This abstract is intended as a scanning tool for purposes of searching in the particular art and is not intended to be limiting of the present invention.

19 Claims, 9 Drawing Sheets

(56) References Cited

OTHER PUBLICATIONS

Bowser TE, et al., Novel anti-infection agents: small molecule inhibitors of bacterial tanscription factors, Bioorg. Med. Chem. Lett., 2007, 17, 5652-5655.
Buhling et al., Influence of anti-Helicobacter triple-therapy with metronidazole, omeprazole and clarithromycin on intestinal microflora, Aliment. Pharm. Ther., 2001, 15(9), 1445-1452.
Cieslak, et al., Clinical and Epidemiologic Principles of Anthrax, CDC Emerg. Infect. Dis., 1999, 5 (4), 552-555.
Database Registry [online] Chemical Abstracts Service, Columbus, OH, US; Nov. 16, 1984 (Nov. 16, 1984), Chemical Abstracts Service Registry No. 145-42-6.
Dayal, B., et al., 1995. Microwave-induced rapid synthesis of sarcosine conjugated bile acids. Bioorg. Med. Chem. Lett. 5(12):1301-1306.
Dodatko, T., M. et al., 2010. Dissecting interactions between nucleosides and germination receptors in Bacillus cereus 569 spores. Microbiology. 156(4):1244-1255.
Foster, S. J. et al., 1990. Pulling the trigger: The mechanism ofbacterial spore germination. Mol. Microbial. 4(1):137-141.
Gargiulo, D., et al. 1989. Synthesis of mosesin-4, a naturally occurring steroid saponin with shark repellent activity, and its analog 7-ß-galactosyl ethyl cholate. Tetrahedron. 45(17):5423-5432.
Gisbert et al. (2005) Systematic review and meta-analysis: proton pump inhibitor vs. ranitidine bismuth citrate plus two antibiotics in Helicobacter pylorieradication. Helicobacter., 2005, 10(3), 157-171.
Grant No. CHE0957400 awarded by the National Science Foundation (Jul. 23, 2009).
Harsch et al. (2001) Pseudomembranous colitis after eradication of Helicobacterpylori infection with a triple therapy. Med. Sci. Monit., 2001, 7(4), 751-754.
Howerton et al., “Mapping Interactions between Germinants and Clostridium difficile Spores,” Journal of Bacteriology, Jan. 2011, p. 274-282.
Iida, T. et al., 1982. Potential bile acid metabolites. 6. Stereoisomeric 3,7-dihydroxy-5ß-cholanic acids. J. Org. Chem 47(15):2966-2972.
Infectious Disease Society of America, 2004, Bad Bugs, No Drugs (35 pages).
Janssen et al. (2001) A systematic comparison of triple therapies for treatment of Helicobacter pylori infection with proton pump inhibitor/ ranitidine bismuth citrate plus clarithromycin and either amoxicillin or a nitroimidazole, Aliment. Pharmacal. Ther., 2001, 15(5), 613-624.
Indu, B., et al., 1993. Methanol-formic acid esterification equilibrium in sulfuric acid solutions: Influence of sodium salts. Ind. Eng. Chem. Res. 32( 5):981-985.
Nawaz et al. (1998) Clostridium difficile colitis associated with treatment of Helicobacter pylori infection. Am. J. Gastroenterol., 1998, 93(7), 1175-1176.
Preston, R. A. et al., 1988. Functional relationships between L- and D-alanine, inosine and NH4Cl during germination of spores of Bacillus cereus. T. J. Gen. Microbial. 134(11):3001-3010.
Ramirez, N. et al., 2010. Requirements for germination of Clostridium sordellii spores in vitro. J. Bacteriol. 192(2):418-425.
Rodbard, D. et al., 1978. Kinetics of two-site immunoradiometric (‘sandwich’) assays. I. Mathematical models for simulation, optimization, and curve fitting. Mol. Immunol. 15(2):71-76.
Rodbard, D.et al., 1977. Automated computer analysis for enzyme multiplied immunological techniques. Clin. Chem. 23(1):112-115.
Sidoova et al., CS 275631 B6 (Mar. 18, 1992) (CAS SciFinder abstract, database CAPLUS Acc No. 1994:270377).
Sorg, J. A. et al., 2008. Bile salts and glycine as cogerminants for Clostridium difficile spores. J. Bacterial. 190(7):2505-2512.
Spellberg et al. (2004) Trends in antimicrobial drug development: implications for the future.Clin. Infect. Dis., 2004, 38, 1279-1286.
Tserng, K. Y., et al., 1977. An improved procedure for the synthesis of glycine and taurine conjugates of bile acids. J. Lipid Res. 18(3):404-407.
International Search Report and Written Opinion mailed on Aug. 11, 2016 by the International Searching Authority for International Patent Application No. PCT/US2016/016848, which was filed on Feb. 5, 2016 and published as WO 2016/127102 on Aug. 11, 2016 (Applicant—Abel-Santos, et al.) (9 pages).
International Preliminary Report on Patentability issued on Aug. 8, 2017 by the International Searching Authority for International Patent Application No. PCT/US2016/016848, which was filed on Feb. 5, 2016 and published as WO 2016/127102 on Aug. 11, 2016 (Applicant—Abel-Santos, et al.) (6 pages).
Requirement for Restriction/Election issued on Sep. 26, 2014 by the USPTO for U.S. Appl. No. 13/962,658, filed Aug. 8, 2013 and granted as U.S. Pat. No. 9,079,935 on Jul. 14, 2015(Applicant—Abel-Santos, et al.) (8 pages).
Response to Requirement for Restriction/Election mailed on Oct. 16, 2014 to the USPTO for U.S. Appl. No. 13/962,658, filed Aug. 8, 2013 and granted as U.S. Pat. No. 9,079,935 on Jul. 14, 2015 (Applicant—Abel-Santos, et al.) (13 pages).
Non Final issued on Oct. 24, 2014 by the USPTO for U.S. Appl. No. 13/962,658, filed Aug. 8, 2013 and granted as U.S. Pat. No. 9,079,935 on Jul. 14, 2015(Applicant—Abel-Santos, et al.) (7 pages).
Response to Non Final issued on Jan. 9, 2015 to the USPTO for U.S. Appl. No. 13/962,658, filed Aug. 8, 2013 and granted as U.S. Pat. No. 9,079,935 on Jul. 14, 2015 (Applicant—Abel-Santos, et al.) (5 pages).
Notice of Allowance issued on Mar. 6, 2015 by the USPTO for U.S. Appl. No. 13/962,658, filed Aug. 8, 2013 and granted as U.S. Pat. No. 9,079,935 on Jul. 14, 2015 (Applicant—Abel-Santos, et al.) (8 pages).
Issue Notification issued on Jun. 24, 2015 by the USPTO for U.S. Appl. No. 13/962,658, filed Aug. 8, 2013 and granted as U.S. Pat. No. 9,079,935 on Jul. 14, 2015 (Applicant—Abel-Santos, et al.) (1 page).
Preliminary Amendment issued on Jul. 13, 2015 by the USPTO for U.S. Appl. No. 14/798,276, filed Jul. 13, 2015 and granted as U.S. Pat. No. 9,862,744 on Jan. 9, 2018 (Applicant—Abel-Santos, et al.) (11 pages).
Requirement for Restriction/Election issued on May 19, 2016 by the USPTO for U.S. Appl. No. 14/798,276, filed Jul. 13, 2015 and granted as U.S. Pat. No. 9,862,744 on Jan. 9, 2018 (Applicant—Abel-Santos, et al.) (7 pages).
Response to Requirement for Restriction/Election mailed on Jul. 5, 2016 to the USPTO for U.S. Appl. No. 14/798,276, filed Jul. 13, 2015 and granted as U.S. Pat. No. 9,862,744 on Jan. 9, 2018 (Applicant—Abel-Santos, et al.) (10 pages).
Non Final Rejection issued on Jul. 18, 2016 by the USPTO for U.S. Appl. No. 14/798,276, filed Jul. 13, 2015 and granted as U.S. Pat. No. 9,862,744 on Jan. 9, 2018 (Applicant—Abel-Santos, et al.) (11 pages).
Response to Non Final Rejection mailed on Oct. 18, 2016 to the USPTO for U.S. Appl. No. 14/798,276, filed Jul. 13, 2015 and granted as U.S. Pat. No. 9,862,744 on Jan. 9, 2018 (Applicant—Abel-Santos, et al.) (12 pages).
Final Rejection issued on Nov. 14, 2016 by the USPTO for U.S. Appl. No. 14/798,276, filed Jul. 13, 2015 and granted as U.S. Pat. No. 9,862,744 on Jan. 9, 2018 (Applicant—Abel-Santos, et al.) (6 pages).
Response to Final Rejection mailed on Feb. 10, 2017 to the USPTO for U.S. Appl. No. 14/798,276, filed Jul. 13, 2015 and granted as U.S. Pat. No. 9,862,744 on Jan. 9, 2018 (Applicant—Abel-Santos, et al.) (8 pages).
Non Final Rejection issued on Mar. 30, 2017 to the USPTO for U.S. Appl. No. 14/798,276, filed Jul. 13, 2015 and granted as U.S. Pat. No. 9,862,744 on Jan. 9, 2018 (Applicant—Abel-Santos, et al.) (12 pages).
Response to Non Final Rejection mailed on Jun. 20, 2017 to the USPTO for U.S. Appl. No. 14/798,276, filed Jul. 13, 2015 and granted as U.S. Pat. No. 9,862,744 on Jan. 9, 2018 (Applicant—Abel-Santos, et al.) (8 pages).

(56) References Cited

OTHER PUBLICATIONS

Notice of Allowance issued on Sep. 7, 2017 to the USPTO for U.S. Appl. No. 14/798,276, filed Jul. 13, 2015 and granted as U.S. Pat. No. 9,862,744 on Jan. 9, 2018 (Applicant—Abel-Santos, et al.) (9 pages).
Issue Notification issued on Dec. 20, 2017 to the USPTO for U.S. Appl. No. 14/798,276, filed Jul. 13, 2015 and granted as U.S. Pat. No. 9,862,744 on Jan. 9, 2018 (Applicant—Abel-Santos, et al.) (1 page).
Preliminary Amendment filed on Jul. 21, 2017 with the U.S. Patent and Trademark Office for U.S. Appl. No. 15/545,645, filed Jul. 21, 2017 and published as US 2018/0000793 on Jan. 4, 2018 (Inventor—Abel-Santos et al.; Applicant—Board of Regents of the Nevada System of High Education on Behalf of the University of Nevada, Las Vegas) (11 pages).
Restriction Requirement issued on Jan. 8, 2018 by the U.S. Patent and Trademark Office for U.S. Appl. No. 15/545,645, filed Jul. 21, 2017 and published as US 2018/0000793 on Jan. 4, 2018 (Inventor—Abel-Santos et al.; Applicant—Board of Regents of the Nevada System of High Education on Behalf of the University of Nevada, Las Vegas) (9 pages).
Non-Final Office Action issued on Apr. 3, 2018 by the U.S. Patent and Trademark Office for U.S. Appl. No. 15/545,645, filed Jul. 21, 2017 and published as US 2018/0000793 on Jan. 4, 2018 (Inventor—Abel-Santos et al.; Applicant—Board of Regents of the Nevada System of High Education on Behalf of the University of Nevada, Las Vegas) (8 pages).
Notice of Allowance issued on Oct. 1, 2018 by the U.S. Patent and Trademark Office for U.S. Appl. No. 15/545,645, filed Jul. 21, 2017 and published as US 2018/0000793 on Jan. 4, 2018 (Inventor—Abel-Santos et al.; Applicant—Board of Regents of the Nevada System of High Education on Behalf of the University of Nevada, Las Vegas) (9 pages).
Garai et al. (2020) "Application of Fluorine- and Nitrogen-Walk Approaches: Defining the Structural and Functional Diversity of 2-Phenylindole Class of CB1 Receptor Positive Allosteric Modulators," *J Med Chem* 63(2): 542-568.
Leverrier et al. (2015) "Structure-activity relationship of hybrids of Cinchona alkaloids and bile acids with in vitro antiplasmodial and antitrypanosomal activities," *European Journal of Medicinal Chemistry* 100: 10-17.
PubChem-SID-104587389 [online] [retrieved on Feb. 22, 2011]. Retrieved from: PubChem: <URL: https://pubchem.ncbi.nlm.nih.gov/substance/104587389>.
Xiong, P. et al., "Site-Selective Electrooxidation of Methylarenes to Aromatic Acetals" Nature Communications, vol. 11 No. 1 Jun. 2020, p. 2706.
Xiong, P. et al., "Site-Selective Electrooxidation of Methylarenes to Aromatic Acetals" Nature Communications, vol. 11 No. 1 Jun. 2020, Supplementary Information.

* cited by examiner

INHIBITING GERMINATION OF CLOSTRIDIUM PERFRINGENS SPORES TO REDUCE NECROTIC ENTERITIS

CROSS-REFERENCE TO RELATED APPLICATIONS

This application is a continuation of U.S. patent application Ser. No. 16/236,919, filed Dec. 31, 2018, which is a continuation of U.S. patent application Ser. No. 15/545,645, filed Jul. 21, 2017, which is a 35 U.S.C. § 371 U.S. National Stage of International Application No. PCT/US2016/016848, filed Feb. 5, 2016, which claims the benefit under 35 U.S.C. § 119 (e) to U.S. Provisional Application No. 62/113,184, filed on Feb. 6, 2015, the contents of which are incorporated herein fully by reference in their entireties.

STATEMENT REGARDING FEDERALLY SPONSORED RESEARCH

This invention was made with government support under Grant no. 2010-65119-20603, awarded by the United States Department of Agriculture. The government has certain rights in the invention.

BACKGROUND

*C. perfringens* is a Gram-positive, rod-shaped, spore-forming, obligate anaerobic bacterium (Van Immerseel et al., *Avian Pathol* 2004, 33 (6): 537-549; Shimizu et al., *Proc Natl Acad Sci USA* 2002, 99 (2): 996-1001: Myers et al., *Genome Res* 2006, 16 (8): 1031-1040; and Petit et al., *Trends Microbiol* 1999, 7 (3): 104-110) that causes a wide range of diseases in humans and animals, ranging from food poisoning to severe invasive disease (e.g., myonecrosis) (Van Immerseel et al., *Trends Microbiol* 2009, 17 (1): 32-36). The ability of *C. perfringens* to cause disease is ascribed mainly to the differential production of four major and ten minor protein toxins (Rood, *Ann Rev Microbiol* 1998, 52 (1): 333-360; and Smedley et al., "The enteric toxins of *Clostridium perfringens*," In: Rev Physiol Biochem Pharmacol 2005:183-204).

In avian species, *C. perfringens* strains can cause necrotic enteritis (NE), which can result in substantial economic damage to commercial poultry (Petit et al., supra). Chickens suffering from clinical NE appear depressed, anorexic, and relatively immobile (Broussard et al., *Avian Dis* 1986, 30 (3): 617-619). Onset of disease is sudden, with death ensuing quickly (Wages and Opengart, "Necrotic enteritis," in *Diseases of Poultry,* 11th ed., Iowa State Press, Ames, I A, 2003). The acute form of NE may cause up to 30% mortality in broiler flocks (Kaldhusdal and Lvland, *World Poultry* 2000a, 16:50-51; and Williams, *Avian Pathol* 2005, 34 (3): 159-180). In the sub-clinical form, damage to the intestinal mucosa can lead to decreased digestion and absorption, reduced weight gain, and a poor feed conversion ratio (Elwinger et al., *Acta Veterinaria Scandinavia* 1992, 33:369-378; and Kaldhusdal et al., *Avian Dis* 2001, 45 (1): 149-156).

*C. perfringens* spores are ubiquitous in the environment, and colonization of poultry by *C. perfringens* occurs early in the life of the animals (Craven et al., *Avian Dis* 2003, 47 (3): 707-711: Craven et al., *Avian Dis* 2001, 45 (4): 887-896; and Barbara et al., *Veterinary Microbiol* 2008, 126 (4): 377-382). Most of these strains, however, are part of the normal flora, and are incapable of initiating the disease process. Thus, the mere presence of *C. perfringens* in the gastrointestinal (GI) tract of broiler chickens is not sufficient for the development of NE (Van Immerseel et al., supra: Kaldhusdal, *World Poultry* 2000b, 16 (6): 42-43; and Hermans and Morgan, *Res Vet Science* 2003, 74 (Suppl. 1): 19). Rather, one or more predisposing factors may be required to elicit the clinical signs and lesions of NE. For example, an important predisposing factor in natural cases of NE may be intestinal damage caused by coccidia (Williams, supra). These organisms can damage enterocytes, opening a pathway for the association of *C. perfringens* with the mucosal epithelium. Coccidia also can alter the normal gut flora (Oviedo-Rondon et al., *Poultry Sci* 2006, 85 (5): 854-860), which can allow for *C. perfringens* spore germination followed by colonization of the empty intestinal niches by the vegetative, toxin-producing cells. Feed composition also is a potent risk factor. In particular, diets based on wheat or barley are far more likely to be associated with outbreaks of NE than are diets based on corn (Kaldhusdal 2000b, supra; and Riddell and Kong, *Avian Dis* 1992, 36 (3): 499-503).

NE infections in the US often are controlled incidentally by in-feed antibiotic growth promoters (AGPs), which include well-known antibacterial and antiparasitic drugs (Williams, supra). The phasing out of antibiotic growth promoters from poultry diets in Europe, however, has changed the microbial profile of the GI tract in commercial poultry (Yegani and Korver, *Poultry Sci* 2008, 87 (10): 2052-2063). In Scandinavian countries, a ban on antimicrobial growth promoters was almost immediately followed by an NE epidemic (Kaldhusdal 2000a, supra), leading to the use of greatly increased amounts of antimicrobials for treatment. In addition, anti-coccidial compounds (mainly ionophores) have been removed from routine use due to the introduction of a highly efficacious attenuated anti-coccidial vaccine (Crouch et al., *Avian Pathol* 2003, 32 (3): 297-304). These ionophore compounds also are anti-clostridial, so their absence from feed can increase the incidence of NE.

Due to the changes in commercial poultry feed supplementation, NE has become a global economic problem (van der Sluis, *World Poultry* 2000, 16 (5): 56-57). Moreover, methods for controlling NE in poultry are not well established (Williams, supra), and most protocols rely on dietary modifications to prevent NE (Riddell and Kong, supra). Although AGPs are effective in clinical NE suppression (Elwinger et al., *Acta Veterinaria Scandinavia* 1998, 39:433-441), prophylactic antibiotic use has been discouraged. Accordingly, there remains a need for methods of reducing, preventing, and/or treating NE in poultry. These needs and others are met by the present invention.

SUMMARY

In accordance with the purpose(s) of the invention, as embodied and broadly described herein, the invention, in one aspect, relates to compounds that can prevent germination of *C. perfringens* spores and materials and methods for reducing or preventing *C. perfringens* spore germination, as well as materials and methods for reducing, preventing, or treating adverse effects associated with exposure to germinated *C. perfringens*, including NE.

Disclosed are methods for preventing a disease caused by infection by *Clostridium perfringens* in a subject, the method comprising administering to the subject an effective amount of a compound having a structure represented by a formula:

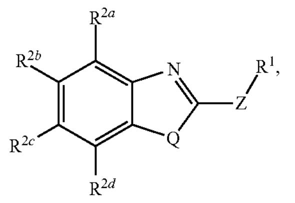

wherein Q is selected from O, S, and $NR^3$; wherein $R^3$, when present, is selected from hydrogen and C1-C8 alkyl; wherein Z is selected from O, S, and $NR^4$; wherein $R^4$, when present, is selected from hydrogen and C1-C8 alkyl; wherein $R^1$ is selected from hydrogen, C1-C8 alkyl, C1-C8 haloalkyl, $—CR^{5a}R^{5b}(C{=}O)NHN{=}CR^6Ar^1$, $Cy^1$, and $Ar^2$, provided that if Q is $NR^3$ then $R^1$ is not $—CR^{5a}R^{5b}(C{=}O)R^5$; wherein each of $R^{5a}$ and $R^{5b}$, when present, is independently selected from hydrogen and C1-C4 alkyl; wherein $R^6$, when present, is selected from hydrogen and C1-C4 alkyl; wherein $Cy^1$ is selected from C3-C7 cycloalkyl and C2-C7 heterocycloalkyl and substituted with 0, 1, or 2 groups independently selected from halogen, —OH, —CN, $—NO_2$, $—NH_2$, C1-C4 alkyl, C1-C4 alkoxy, C1-C4 haloalkyl, C1-C4 alkylamino, and (C1-C4)(C1-C4) dialkylamino; wherein $Ar^1$ is selected from aryl and heteroaryl and substituted with 0, 1, or 2 groups independently selected from halogen, —OH, —CN, $—NO_2$, $—NH_2$, C1-C4 alkyl, C1-C4 alkoxy, C1-C4 haloalkyl, C1-C4 alkylamino, and (C1-C4)(C1-C4) dialkylamino; wherein $Ar^2$ is selected from aryl and heteroaryl and substituted with 0, 1, or 2 groups independently selected from halogen, —OH, —CN, $—NO_2$, $—NH_2$, C1-C4 alkyl, C1-C4 alkoxy, C1-C4 haloalkyl, C1-C4 alkylamino, and (C1-C4)(C1-C4) dialkylamino; and wherein each of $R^{2a}$, $R^{2b}$, $R^{2c}$, and $R^{2d}$ is independently selected from hydrogen, halogen, —OH, —CN, $—NO_2$, $—NH_2$, C1-C4 alkyl, C1-C4 alkoxy, C1-C4 haloalkyl, C1-C4 alkylamino, and (C1-C4)(C1-C4) dialkylamino, thereby preventing the disease caused by infection by *Clostridium perfringens* in a subject.

Also disclosed are methods for inhibiting germination of at least one *Clostridium perfringens* spore, the method comprising contacting the spore with a compound having a structure represented by a formula:

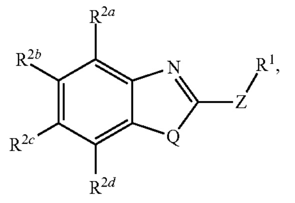

wherein Q is selected from O, S, and $NR^3$; wherein $R^3$, when present, is selected from hydrogen and C1-C8 alkyl; wherein Z is selected from O, S, and $NR^4$; wherein $R^4$, when present, is selected from hydrogen and C1-C8 alkyl; wherein $R^1$ is selected from hydrogen, C1-C8 alkyl, C1-C8 haloalkyl, $—CR^{5a}R^{5b}(C{=}O)NHN{=}CR^6Ar^1$, $Cy^1$, and $Ar^2$, provided that if Q is $NR^3$ then $R^1$ is not $—CR^{5a}R^{5b}(C{=}O)R^5$; wherein each of $R^{5a}$ and $R^{5b}$, when present, is independently selected from hydrogen and C1-C4 alkyl; wherein $R^6$, when present, is selected from hydrogen and C1-C4 alkyl; wherein $Cy^1$ is selected from C3-C7 cycloalkyl and C2-C7 heterocycloalkyl and substituted with 0, 1, or 2 groups independently selected from halogen, —OH, —CN, $—NO_2$, $—NH_2$, C1-C4 alkyl, C1-C4 alkoxy, C1-C4 haloalkyl, C1-C4 alkylamino, and (C1-C4)(C1-C4) dialkylamino; wherein $Ar^1$ is selected from aryl and heteroaryl and substituted with 0, 1, or 2 groups independently selected from halogen, —OH, —CN, $—NO_2$, $—NH_2$, C1-C4 alkyl, C1-C4 alkoxy, C1-C4 haloalkyl, C1-C4 alkylamino, and (C1-C4)(C1-C4) dialkylamino; wherein $Ar^2$ is selected from aryl and heteroaryl and substituted with 0, 1, or 2 groups independently selected from halogen, —OH, —CN, $—NO_2$, $—NH_2$, C1-C4 alkyl, C1-C4 alkoxy, C1-C4 haloalkyl, C1-C4 alkylamino, and (C1-C4)(C1-C4) dialkylamino; and wherein each of $R^{2a}$, $R^{2b}$, $R^{2c}$, and $R^{2d}$ is independently selected from hydrogen, halogen, —OH, —CN, $—NO_2$, $—NH_2$, C1-C4 alkyl, C1-C4 alkoxy, C1-C4 haloalkyl, C1-C4 alkylamino, and (C1-C4)(C1-C4) dialkylamino, thereby inhibiting germination of at least one *Clostridium perfringens* spore.

Also disclosed are feed compositions comprising feed components and a compound having a structure represented by a formula:

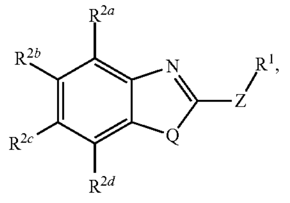

wherein Q is selected from O, S, and $NR^3$; wherein $R^3$, when present, is selected from hydrogen and C1-C8 alkyl; wherein Z is selected from O, S, and $NR^4$; wherein $R^4$, when present, is selected from hydrogen and C1-C8 alkyl; wherein $R^1$ is selected from hydrogen, C1-C8 alkyl, C1-C8 haloalkyl, $—CR^{5a}R^{5b}(C{=}O)NHN{=}CR^6Ar^1$, $Cy^1$, and $Ar^2$, provided that if Q is $NR^3$ then $R^1$ is not $—CR^{5a}R^{5b}(C{=}O)R^5$; wherein each of $R^{5a}$ and $R^{5b}$, when present, is independently selected from hydrogen and C1-C4 alkyl; wherein $R^6$, when present, is selected from hydrogen and C1-C4 alkyl; wherein $Cy^1$ is selected from C3-C7 cycloalkyl and C2-C7 heterocycloalkyl and substituted with 0, 1, or 2 groups independently selected from halogen, —OH, —CN, $—NO_2$, $—NH_2$, C1-C4 alkyl, C1-C4 alkoxy, C1-C4 haloalkyl, C1-C4 alkylamino, and (C1-C4)(C1-C4) dialkylamino; wherein $Ar^1$ is selected from aryl and heteroaryl and substituted with 0, 1, or 2 groups independently selected from halogen, —OH, —CN, $—NO_2$, $—NH_2$, C1-C4 alkyl, C1-C4 alkoxy, C1-C4 haloalkyl, C1-C4 alkylamino, and (C1-C4)(C1-C4) dialkylamino; wherein $Ar^2$ is selected from aryl and heteroaryl and substituted with 0, 1, or 2 groups independently selected from halogen, —OH, —CN, $—NO_2$, $—NH_2$, C1-C4 alkyl, C1-C4 alkoxy, C1-C4 haloalkyl, C1-C4 alkylamino, and (C1-C4)(C1-C4) dialkylamino; and wherein each of $R^{2a}$, $R^{2b}$, $R^{2c}$, and $R^{2d}$ is independently selected from hydrogen, halogen, —OH, —CN, $—NO_2$, $—NH_2$, C1-C4 alkyl, C1-C4 alkoxy, C1-C4 haloalkyl, C1-C4 alkylamino, and (C1-C4)(C1-C4) dialkylamino.

Also disclosed are compositions containing a compound that, when administered to an animal, inhibits germination of *Clostridium perfringens* spores in the gut of the animal. The compound can be a compound of Formula (I):

(I)

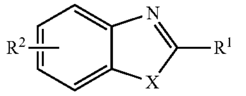

wherein X is selected from the group consisting of O, N, and S, and $R^1$ and $R^2$ independently are selected from the group consisting of H, OH, CN, $NO_2$, halo, $C_{1-3}$ alkyl, $C_{1-3}$ haloalkyl, $C_{1-3}$ alkoxy, $C_{1-3}$ haloalkoxy, $C_{3-7}$ cycloalkyl, amino, $C_{1-3}$ alkylamino, and di($C_{1-3}$ alkyl)amino. Alternatively, the compound can be MOB:

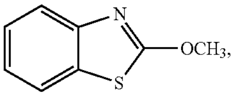 [SMILES: COc1nc2ccccc2s1]

or a pharmaceutically acceptable salt thereof, or the compound can be 2-MTB:

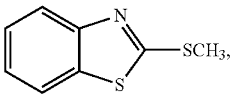 [SMILES: CSc1nc2ccccc2s1]

or a pharmaceutically acceptable salt thereof. The animal can be a farm animal (e.g., a chicken, turkey, duck, goose, cow, sheep, horse, or pig). The composition can be formulated as feed for the animal.

Also disclosed are methods for inhibiting germination of a *Clostridium perfringens* spore, comprising contacting the spore with a composition containing MOB or a pharmaceutically acceptable salt thereof, 2-MTB or a pharmaceutically acceptable salt thereof. The spore can be in the gut of an animal. The animal can be a farm animal (e.g., a chicken, turkey, duck, goose, cow, sheep, horse, or pig).

Also disclosed are methods for reducing the occurrence of necrotizing enteritis in a population of animals, comprising administering to the population a composition containing MOB or a pharmaceutically acceptable salt thereof, or 2-MTB or a pharmaceutically acceptable salt thereof, wherein the compound is administered in an amount effective to prevent germination of *Clostridium perfringens* spores in the gut of at least one member of the population. The population can be a population of chickens, turkeys, ducks, geese, cattle, sheep, horses, or pigs. The method can include administering the compound via feed provided to the population.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

The accompanying figures, which are incorporated in and constitute a part of this specification, illustrate several aspects and together with the description serve to explain the principles of the invention.

FIG. 2A shows a representative graph plotting germination of *C. perfringens* spores in defined medium (open circles) or in a solution containing 25 mM L-alanine, 5 mM L-phenylalanine and 50 mM $NaHCO_3$ (filled circles), as followed by the decrease in optical density at 580 nm (OD580). For clarity, data are shown at 5 minute intervals. The data were generated for spores from *C. perfringens* strain JGS 1936. Other *C. perfringens* strains yielded similar results. FIG. 2B shows a representative graph plotting relative germination rates for *C. perfringens* JGS 1936 spores treated with the indicated amino acid mixtures. Germination rates were calculated from the linear segment of optical density changes over time. Relative germination was calculated as the fraction of the germination rate for spores treated with L-alanine/L-phenylalanine. Amino acids are represented by the one-letter code. Error bars represent standard deviations of six independent measurements. *$p<0.003$ compared to L-alanine/L-phenylalanine.

FIG. 3A shows a representative graph plotting relative germination of *C. perfringens* JGS 1936 spores treated with taurocholate and the indicated individual amino acids. Relative germination was calculated as the fraction of the germination rate for spores treated with L-alanine/taurocholate. Amino acids are represented by one-letter code. Error bars represent standard deviations of six independent measurements. FIG. 3B shows a representative graph plotting relative germination of *C. perfringens* JGS 1936 spores treated with L-alanine and individual bile salts. Relative germination was calculated as the fraction of the germination rate for spores treated with L-alanine/taurocholate. Error bars represent standard deviations of six independent measurements.

FIG. 4A shows a representative graph plotting relative germination of *C. perfringens* JGS 1936 spores treated with L-alanine and L-phenylalanine at different pH levels in sodium phosphate buffer (open circles) or potassium phosphate buffer (filled circles). Relative germination was calculated as the fraction of the germination rate for spores suspended in sodium phosphate buffer, pH=6.5. Error bars represent standard deviations of six independent measurements. FIG. 4B shows a representative graph plotting relative germination of *C. perfringens* JGS 1936 spores treated with taurocholate and L-alanine at different pH levels in sodium phosphate buffer (open circles) or potassium phosphate buffer (filled circles). Relative germination was calculated as the fraction of the germination rate for spores suspended in potassium phosphate buffer, pH=6.5. FIG. 4C shows a representative graph plotting relative germination of *C. perfringens* JGS 1936 spores resuspended in either sodium phosphate (white bars) or potassium phosphate (black bars). Samples were individually supplemented with KCl, KBr, NaCl, NaBr, $KHCO_3$, or $NaHCO_3$. Germination was initiated by addition of L-alanine and L-phenylalanine. Relative germination was calculated as the fraction of the germination rate for spores suspended in sodium phosphate buffer, pH=6.5. FIG. 4D shows a representative graph plotting relative germination rate for *C. perfringens* JGS 1936 spores resuspended in either sodium phosphate (white bars) or potassium phosphate (black bars). Samples were individually supplemented with KCl, KBr, NaCl, NaBr, $KHCO_3$, or $NaHCO_3$. Germination was initiated by addition of taurocholate and L-alanine. Relative germination was calculated as the fraction of the germination rate for spores suspended in potassium phosphate buffer, pH=6.5.

Figure 1:
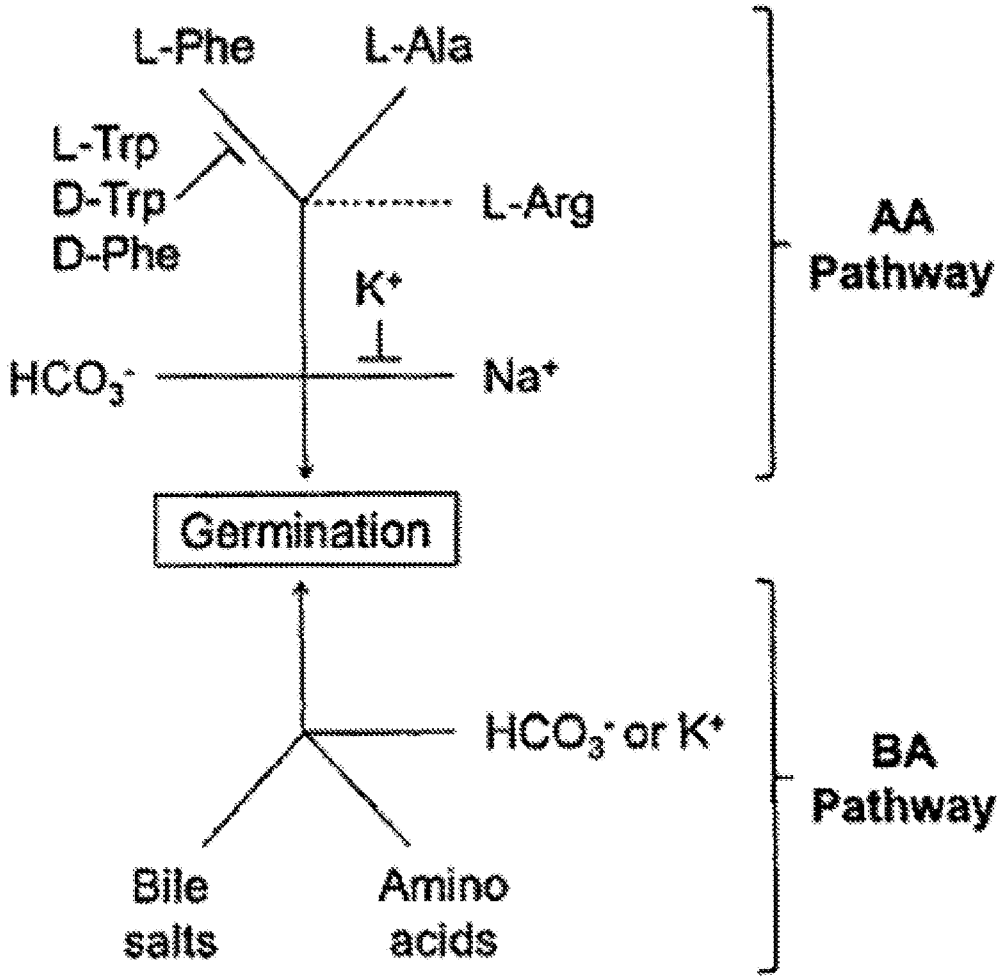
FIG. 1 shows a representative diagram of a scheme for *C. perfringens* spore germination. Solid lines represent required co-germinants. Capped lines represent germination inhibitors. Dashed lines represent germination enhancers.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein may be different from the actual publication dates, which can require independent confirmation.

A. Definitions

As used in the specification and the appended claims, the singular forms "a," "an" and "the" include plural referents unless the context clearly dictates otherwise. Thus, for example, reference to "a functional group." "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or cannot occur, and that the description includes instances where said event or circumstance occurs and instances where it does not.

It is appreciated that certain features of the disclosure, which are, for clarity, described in the context of separate aspects, can also be provided in combination in a single aspect. Conversely, various features of the disclosure which are, for brevity, described in the context of a single aspect, can also be provided separately or in any suitable subcombination.

For the terms "for example" and "such as," and grammatical equivalents thereof, the phrase "and without limitation" is understood to follow unless explicitly stated otherwise. All measurements reported herein are understood to be modified by the term "about", whether or not the term is explicitly used, unless explicitly stated otherwise.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

All compounds, and salts thereof (e.g., pharmaceutically acceptable salts), can be found together with other substances such as water and solvents (e.g., hydrates and solvates).

Compounds provided herein also can include tautomeric forms. Tautomeric forms result from the swapping of a single bond with an adjacent double bond together with the concomitant migration of a proton. Tautomeric forms include prototropic tautomers that are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds provided herein can also include all isotopes of atoms occurring in the intermediates or final compounds. Isotopes include those atoms having the same atomic number but different mass numbers. For example, isotopes of hydrogen include hydrogen, tritium, and deuterium.

The phrase "pharmaceutically acceptable" is used herein to refer to those compounds, materials, compositions, and/or dosage forms that are, within the scope of sound medical judgment, suitable for use in contact with the tissues of human beings and animals without excessive toxicity, irritation, allergic response, or other problem or complication, commensurate with a reasonable benefit/risk ratio.

Also provided herein are pharmaceutically acceptable salts of the compounds described herein. As used herein, the term "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the compounds provided herein include the conventional non-toxic salts of the parent compound formed, for example, from non-toxic inorganic or organic acids. The pharmaceutically acceptable salts of the compounds provided herein can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. In various aspects, a non-aqueous media like ether, ethyl acetate, alcohols (e.g., methanol, ethanol, iso-propanol, or butanol) or acetonitrile (ACN) can be used. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977). Conventional methods for preparing salt forms are described, for example, in *Handbook of Pharmaceutical Salts: Properties. Selection, and Use*, Wiley-VCH, 2002.

In some embodiments, a compound provided herein, or salt thereof, is substantially isolated. By "substantially isolated" is meant that the compound is at least partially or substantially separated from the environment in which it was formed or detected. Partial separation can include, for example, a composition enriched in the compound provided herein. Substantial separation can include compositions containing at least about 50%, at least about 60%, at least about 70%, at least about 80%, at least about 90%, at least about 95%, at least about 97%, or at least about 99% by weight of the compounds provided herein, or salt thereof. Methods for isolating compounds and their salts are routine in the art.

As used herein, chemical structures that contain one or more stereocenters depicted with dashed and bold bonds (i.e., ) are meant to indicate absolute stereochemistry of the stereocenter(s) present in the chemical structure. As used herein, bonds symbolized by a simple line do not indicate a stereo-preference. Unless otherwise indicated to the contrary, chemical structures, which include one or more stereocenters, illustrated herein without indicating absolute or relative stereochemistry encompass all possible stereoisomeric forms of the compound (e.g., diastereomers and enantiomers) and mixtures thereof. Structures with a single bold or dashed line, and at least one additional simple line, encompass a single enantiomeric series of all possible diastereomers.

Resolution of racemic mixtures of compounds can be carried out using appropriate methods. An exemplary method includes fractional recrystallization using a chiral resolving acid that is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid, or the various optically active camphorsulfonic acids such as camphorsulfonic acid. Other resolving agents suitable for fractional crystallization methods include stereoisomerically pure forms of methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent compositions can be determined by one skilled in the art.

The expressions "ambient temperature" and "room temperature" as used herein are understood in the art and refer generally to a temperature, e.g., a reaction temperature, that is about the temperature of the room in which the reaction is carried out, for example, a temperature from about 20° C. to about 30° C.

At various places in the present specification, divalent linking substituents are described. It is specifically intended that each divalent linking substituent include both the forward and backward forms of the linking substituent. For example, —NR(CR'R")$_n$— includes both —NR(CR'R")$_n$— and —(CR'R")$_n$NR—. Where the structure clearly requires a linking group, the Markush variables listed for that group are understood to be linking groups.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

As used herein, the phrase "optionally substituted" means unsubstituted or substituted. As used herein, the term "substituted" means that a hydrogen atom is removed and replaced by a substituent. It is to be understood that substitution at a given atom is limited by valency.

The term "alkyl" includes substituted or unsubstituted straight-chain alkyl groups (e.g., methyl, ethyl, propyl, butyl, pentyl, hexyl, heptyl, octyl, nonyl, decyl, etc.) and branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl, etc.), alkyl substituted cycloalkyl groups, and cycloalkyl substituted alkyl groups. In certain embodiments, a straight chain or branched chain alkyl has six or fewer carbon atoms in its backbone (e.g., $C_{1-6}$ for straight chain; $C_{3-6}$ for branched chain). The term $C_{1-6}$ includes alkyl groups containing 1 to 6 carbon atoms. In certain embodiments, a straight chain alkyl has three or fewer carbon atoms in its backbone. The term $C_{1-3}$ includes alkyl groups containing one to three carbon atoms.

As used herein, "haloalkyl" means a hydrocarbon substituent, which is a linear or branched or cyclic alkyl, alkenyl or alkynyl substituted with one or more chloro, bromo, fluoro, or iodo atom(s). In some embodiments, a haloalkyl is a fluoroalkyl, wherein one or more of the hydrogen atoms have been substituted by fluoro. In some embodiments, haloalkyls are one to about three carbons in length (e.g., one to about two carbons in length, or one carbon in length).

The term "alkoxy" includes groups of the formula-OR, where R is an alkyl as defined herein. Non-limiting examples of alkoxy groups include methoxy, ethoxy, isopropoxy, tert-butoxy, and the like. In some embodiments, an alkoxy group can have from one to three carbons (e.g., methyoxy, ethoxy, or propoxy).

The term "haloalkoxy" includes group of the formula-OR, where R is a haloalkyl as defined herein. Examples of haloalkoxy groups include, without limitation, trifluoromethoxy, difluoromethoxy, etc.

"Alkylamino" includes groups of the formula-NR, where R is an alkyl as defined herein. Non-limiting examples of alkylamino groups include methylamino, ethylamino, isopropylamino, butylamino etc. In some embodiments, an alkylamino group can have from one to three carbons (e.g., methyoxy, ethoxy, or propoxy). The term "dialkylamino" includes groups of the formula —$NR_2$, where R is an alkyl as defined herein. In some embodiments, the alkyl groups of a dialkylamino independently can have one to three carbons.

In general, the term "aryl" includes substituted or unsubstituted aromatic rings, including 5- and 6-membered single-ring aromatic groups, such as benzene and phenyl. Further, the term "aryl" includes multicyclic aryl groups, e.g., tricyclic, bicyclic, such as naphthalene and anthracene. In some embodiments, aryls can have from six to ten (e.g., six, seven, eight, nine, or ten) ring atoms.

The term "heteroaryl" means a substituted or unsubstituted mono-, bi-, tri- or polycyclic group having four to 14 ring atoms, alternatively five, six, nine, or ten ring atoms; having six, ten, or 14 pi electrons shared in a cyclic array; wherein at least one ring in the system is aromatic, and at least one ring in the system contains one or more heteroatoms independently selected from the group consisting of N, O, and S. Exemplary heteroaryl groups include, for example, pyrrole, furan, thiophene, thiazole, isothiaozole, imidazole, triazole, tetrazole, pyrazole, oxazole, isooxazole, pyridine, pyrazine, pyridazine, and pyrimidine, and the like. Further, the term "heteroaryl" includes multicyclic heteroaryl groups, e.g., tricyclic or bicyclic groups, such as benzoxazole, benzodioxazole, benzothiazole, benzoimidazole, benzothiophene, methylenedioxyphenyl, quinoline, isoquinoline, napthyridine, indole, benzofuran, purine, benzofuran, quinazoline, deazapurine, indazole, or indolizine.

The term "heterocycloalkyl" includes substituted or unsubstituted groups, including but not limited to, three- to ten-membered single or multiple rings having one to five heteroatoms, for example, piperazine, pyrrolidine, piperidine, or homopiperazine. In certain embodiments, a heterocycloalkyl can have from four to ten ring atoms.

Methods for making compounds as described herein include those known in the art; such compounds also may be obtained commercially (e.g., from Sigma-Aldrich, St. Louis, MO). In some embodiments, benzoazole derivatives can be generated by modifying the benzyl ring, azole ring, and/or side chain of MOB or 2-MTB, as indicated in Formula (I). Derivatives can include, for example, various benzoimidazoles (where X═N), benzoxazoles (where X═O), and benzothiazoles (where X═S). The derivative compounds can be tested for anti-germination activity, and then tested as NE prophylactics. Information gathered from such in vitro and in vivo screens can be used to direct further derivatization.

The term "substituted" means that an atom or group of atoms replaces hydrogen as a "substituent" attached to another group. For aryl and heteroaryl groups, the term "substituted", unless otherwise indicated, refers to any level of substitution, namely mono, di, tri, tetra, or penta substitution, where such substitution is permitted. The substituents are independently selected, and substitution may be at any chemically accessible position. In some cases, two sites of substitution may come together to form a 3-10 membered cycloalkyl or heterocycloalkyl ring. Non-limiting examples of substituents include: ($C_1$-$C_6$)alkyl, halo, ($C_1$-$C_6$)haloalkyl, —CN, —$NR^8R^9$, —$NO_2$, —O($C_1$-$C_6$)haloalkyl, —$OR^8$, —OC(O)$R^8$, —C(O)$R^8$, —C(O)O$R^8$, —C(O)$NR^8R^9$, —$SR^8$, —S(O)$R^8$, —$SO_2R^8$, —$SO_2NR^8R^9$, ($C_3$-$C_7$) cycloalkyl, ($C_3$-$C_7$)heterocycloalkyl, ($C_5$-$C_{14}$)aryl, and (C5-C14)heteroaryl, wherein $R^8$ and $R^9$ are independently selected from H and ($C_1$-$C_6$)alkyl.

It is to be noted that this document encompasses not only the various isomers of the compounds that may exist, but also the various mixtures of isomers that may be formed, as well as any enantiomers and tautomers that may exist.

In addition, the scope of this document also encompasses solvates and salts of the compounds described herein, as well as prodrugs of the compounds, such as esters, amides, and acylated groups, among others. In some embodiments, for example, this document provides prodrugs of the compounds disclosed herein, which may contain, for example, acylated phenols or acyl derivatives of amines. By "prodrug" is meant, for example, any compound (whether itself active or inactive) that is converted chemically in vivo into a biologically active compound as provided herein, following administration of the prodrug to a subject. In some embodiments, a prodrug is a covalently bonded carrier that releases the active parent drug when administered to a subject. Prodrugs can be prepared by modifying functional groups present in the compounds in such a way that the modifications are cleaved, either in routine manipulation or in vivo, to the parent compounds. Prodrugs can include compounds in which hydroxyl, amino, sulfhydryl, or carboxyl groups are bonded to any group that, when administered to a mammalian subject, cleaves to form a free hydroxyl, amino, sulfhydryl, or carboxyl group respectively. Examples of prodrugs include, without limitation, acetate, formate and benzoate derivatives of alcohol and amine functional groups in the compounds provided herein. The suitability and techniques involved in making and using prodrugs are discussed in Higuchi and Stella, "Pro-drugs as Novel Delivery Systems," Vol. 14 of the ACS Symposium Series, and in *Bioreversible Carriers in Drug Design*, ed. Edward B. Roche, American Pharmaceutical Association and Pergamon Press, 1987, both of which are hereby incorporated by reference in their entirety.

The phrase "pharmaceutically acceptable" is used herein to refer to those compounds, materials, compositions, and/or dosage forms that are, within the scope of sound medical judgment, suitable for use in contact with the tissues of animals without excessive toxicity, irritation, allergic response, or other problem or complication, commensurate with a reasonable benefit/risk ratio. Examples of pharmaceutically acceptable salts of the compounds provided herein include acid addition salts and base salts of the compounds.

B. Compounds

In one aspect, the invention relates to compounds useful in preventing diseases associated with infection caused by *C. perfringens*, in particular necrotizing enteritis. Thus, this document provides compounds for preventing, treating, or reducing NE in fowl and other farmed animals. The compounds can be, for example, MOB and 2-MTB, as shown below.

(MOB)

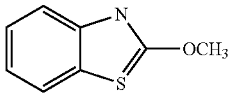

(2-MTB)

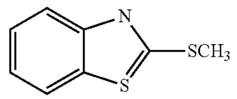

Alternatively, the compounds can be, for example, a benzoazole compound that is a derivative of MOB and/or 2-MTB. Such derivatives can include, without limitation, derivatization of the benzyl ring, the S in the azole ring, and/or the carbon between the S and N within the azole ring. Thus, in various aspects, a compound can be a compound of Formula (I):

(I)

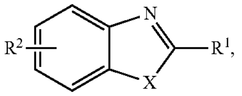

where X can be selected from the group consisting of O, N, and S, and $R^1$ and $R^2$ independently can be selected from the group consisting of H, OH, CN, $NO_2$, halo, $C_{1-3}$ alkyl, $C_{1-3}$ haloalkyl, $C_{1-3}$ alkoxy, $C_{1-3}$ haloalkoxy, $C_{3-7}$ cycloalkyl, amino, $C_{1-3}$ alkylamino, and di($C_{1-3}$ alkyl)amino.

In one aspect, the disclosed compounds exhibit inhibition of germination of *C. perfringens* spores.

In one aspect, the compounds of the invention are useful in the prevention of diseases associated with infection caused by *C. perfringens*, as further described herein.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

1. Structure

In one aspect, disclosed are compounds having a structure represented by a formula:

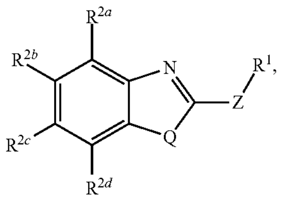

wherein Q is selected from O, S, and $NR^3$; wherein $R^3$, when present, is selected from hydrogen and C1-C8 alkyl; wherein Z is selected from O, S, and $NR^4$; wherein $R^4$, when present, is selected from hydrogen and C1-C8 alkyl; wherein $R^1$ is selected from hydrogen, C1-C8 alkyl, C1-C8 haloalkyl, —$CR^{5a}R^{5b}$(C═O)NHN═$CR^6Ar^1$, $Cy^1$, and $Ar^2$, provided that if Q is $NR^3$ then $R^1$ is not —$CR^{5a}R^{5b}$(C═O)$R^5$; wherein each of $R^{5a}$ and $R^{5b}$, when present, is independently selected from hydrogen and C1-C4 alkyl; wherein $R^6$, when present, is selected from hydrogen and C1-C4 alkyl; wherein $Cy^1$ is selected from C3-C7 cycloalkyl and C2-C7 heterocycloalkyl and substituted with 0, 1, or 2 groups independently selected from halogen, —OH, —CN, —$NO_2$, —$NH_2$, C1-C4 alkyl, C1-C4 alkoxy, C1-C4 haloalkyl, C1-C4 alkylamino, and (C1-C4)(C1-C4) dialkylamino; wherein $Ar^1$ is selected from aryl and heteroaryl and substituted with 0, 1, or 2 groups independently selected from halogen, —OH, —CN, —$NO_2$, —$NH_2$, C1-C4 alkyl, C1-C4 alkoxy, C1-C4 haloalkyl, C1-C4 alkylamino, and (C1-C4)(C1-C4) dialkylamino; wherein $Ar^2$ is selected from aryl and heteroaryl and substituted with 0, 1, or 2 groups independently selected from halogen, —OH, —CN, —$NO_2$, —$NH_2$, C1-C4 alkyl, C1-C4 alkoxy, C1-C4 haloalkyl, C1-C4 alkylamino, and (C1-C4)(C1-C4) dialkylamino; and wherein each of $R^{2a}$, $R^{2b}$, $R^{2c}$, and $R^{2d}$ is independently selected from hydrogen, halogen, —OH, —CN, —$NO_2$, —$NH_2$, C1-C4 alkyl, C1-C4 alkoxy, C1-C4 haloalkyl, C1-C4 alkylamino, and (C1-C4)(C1-C4) dialkylamino.

In a further aspect, Z is selected from O and $NR^4$; wherein $R^1$ is selected from hydrogen, C1-C3 alkyl, and C1-C3 haloalkyl; wherein each of $R^{2a}$, $R^{2b}$, $R^{2c}$, and $R^{2d}$ is independently selected from hydrogen, halogen, —OH, —CN, —$NO_2$, —$NH_2$, C1-C3 alkyl, C1-C3 alkoxy, C1-C3 haloalkyl, C1-C3 alkylamino, and (C1-C3)(C1-C3) dialkylamino; and wherein $R^4$, when present, is selected from hydrogen and C1-C3 alkyl.

In a further aspect, the compound has a structure represented by a formula selected from:

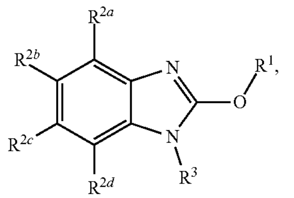

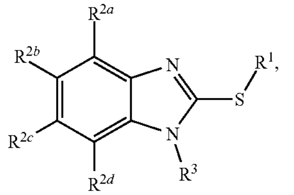

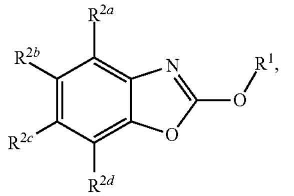

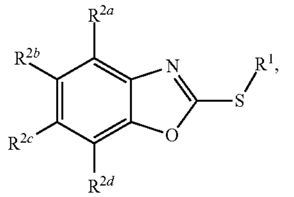

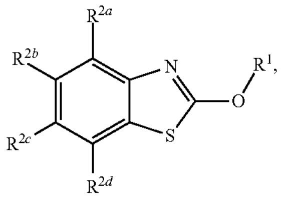

and

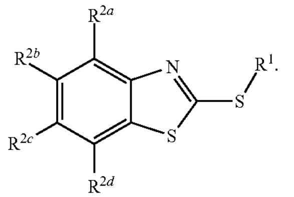

In a further aspect, the compound has a structure represented by a formula selected from:

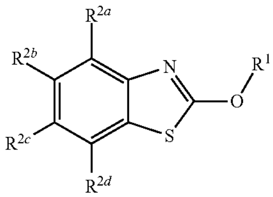

and

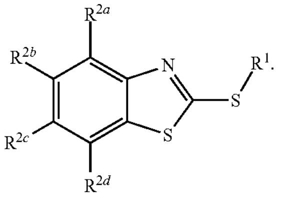

In a further aspect, the compound has a structure represented by a formula selected from:

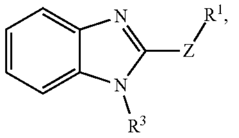

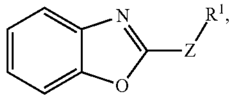

and

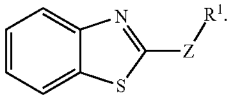

In a further aspect, the compound has a structure represented by a formula:

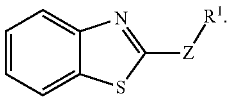

In a further aspect, the compound is selected from:

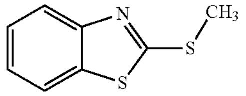

and

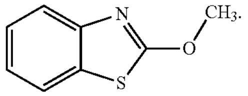

a. Q Groups

In one aspect, Q is selected from O, S, and $NR^3$. In a further aspect, Q is selected from O and $NR^3$. In a still further aspect, Q is selected from S and $NR^3$. In yet a further aspect, Q is selected from O and S. In an even further aspect, Q is O. In a still further aspect, Qis S. In yet a further aspect, Q is $NR^3$.

b. Z Groups

In one aspect, Z is selected from O, S, and $NR^4$. In a further aspect, Z is selected from O and $NR^4$. In a still further aspect, Z is selected from S and $NR^4$. In yet a further aspect, Z is selected from O and S. In an even further aspect, Z is O. In a still further aspect, Z is S. In yet a further aspect, Z is $NR^4$.

c. $R^1$ Groups

In one aspect, $R^1$ is selected from hydrogen, C1-C8 alkyl, C1-C8 haloalkyl, —$CR^{5a}R^{5b}$(C═O)NHN═$CR^6Ar^1$, $Cy^1$, and $Ar^2$, provided that if Q is $NR^3$ then $R^1$ is not-$CR^{5a}R^{5b}$ (C═O)$R^5$. In a further aspect, $R^1$ is selected from hydrogen, C1-C4 alkyl, C1-C4 haloalkyl, —$CR^{5a}R^{5b}$(C═O)NHN═$CR^6Ar^1$, $Cy^1$, and $Ar^2$. In a still further aspect, $R^1$ is hydrogen.

In a further aspect, $R^1$ is selected from —$CR^{5a}R^{5b}$(C═O)NHN═$CR^6Ar^1$, $Cy^1$, and $Ar^2$. In a still further aspect, $R^1$ is selected from $Cy^1$ and $Ar^2$. In yet a further aspect, $R^1$ is $Cy^1$. In a still further aspect, $R^1$ is $Ar^2$. In yet a further aspect, $R^1$ is —$CR^{5a}R^{5b}$(C═O)NHN═$CR^6Ar^1$.

In a further aspect, $R^1$ is selected from hydrogen, C1-C8 alkyl, C1-C8 haloalkyl, $Cy^1$, and $Ar^2$. In a still further aspect, $R^1$ is selected from hydrogen, C1-C4 alkyl, C1-C4 haloalkyl, $Cy^1$, and $Ar^2$. In yet a further aspect, $R^1$ is selected from hydrogen, methyl, ethyl, n-propyl, i-propyl, —$CH_2F$, —$CH_2Cl$, —$CH_2Br$, —$CH_2CH_2F$, —$CH_2CH_2Cl$, —$CH_2CH_2Br$, —$(CH_2)_2CH_2F$, —$(CH_2)_2CH_2Cl$, —$(CH_2)_2CH_2Br$, —$CHF_2$, —$CF_3$, —$CHCl_2$, —$CCl_3$, —$CHBr_2$, —$CBr_3$, —$CH_2CHF_2$, —$CH_2CF_3$, —$CH_2CHCl_2$, —$CH_2CCl_3$, —$CH_2CHBr_2$, —$CH_2CBr_3$, —$(CH_2)_2CHF_2$, —$(CH_2)_2CF_3$, —$(CH_2)_2CHCl_2$, —$(CH_2)_2CCl_3$, —$(CH_2)_2CHBr_2$, —$(CH_2)_2CBr_3$, $Cy^1$, and $Ar^2$. In an even further aspect, $R^1$ is selected from hydrogen, methyl, ethyl, —$CH_2F$, —$CH_2Cl$, —$CH_2Br$, —$CH_2CH_2F$, —$CH_2CH_2Cl$, —$CH_2CH_2Br$, —$CHF_2$, —$CF_3$, —$CHCl_2$, —$CCl_3$, —$CHBr_2$, —$CBr_3$, —$CH_2CHF_2$, —$CH_2CF_3$, —$CH_2CHCl_2$, —$CH_2CCl_3$, —$CH_2CHBr_2$, —$CH_2CBr_3$, $Cy^1$, and $Ar^2$. In a still further aspect, $R^1$ is selected from hydrogen, methyl, —$CH_2F$, —$CH_2Cl$, —$CH_2Br$, —$CHF_2$, —$CF_3$, —$CHCl_2$, —$CCl_3$, —$CHBr_2$, —$CBr_3$, $Cy^1$, and $Ar^2$.

In a further aspect, $R^1$ is selected from hydrogen, C1-C8 alkyl, and C1-C8 haloalkyl. In a still further aspect, $R^1$ is selected from hydrogen, C1-C4 alkyl, and C1-C4 haloalkyl. In yet a further aspect, $R^1$ is selected from hydrogen, methyl, ethyl, n-propyl, i-propyl, —$CH_2F$, —$CH_2Cl$, —$CH_2Br$, —$CH_2CH_2F$, —$CH_2CH_2Cl$, —$CH_2CH_2Br$, —$(CH_2)_2CH_2F$, —$(CH_2)_2CH_2Cl$, —$(CH_2)_2CH_2Br$, —$CHF_2$, —$CF_3$, —$CHCl_2$, —$CCl_3$, —$CHBr_2$, —$CBr_3$, —$CH_2CHF_2$, —$CH_2CF_3$, —$CH_2CHCl_2$, —$CH_2CCl_3$, —$CH_2CHBr_2$, —$CH_2CBr_3$, —$(CH_2)_2CHF_2$, —$(CH_2)_2CF_3$, —$(CH_2)_2CHCl_2$, —$(CH_2)_2CCl_3$, —$(CH_2)_2CHBr_2$, and —$(CH_2)_2CBr_3$. In an even further aspect, $R^1$ is selected from hydrogen, methyl, ethyl, —$CH_2F$, —$CH_2Cl$, —$CH_2Br$, —$CH_2CH_2F$, —$CH_2CH_2Cl$, —$CH_2CH_2Br$, —$CHF_2$, —$CF_3$, —$CHCl_2$, —$CCl_3$, —$CHBr_2$, —$CBr_3$, —$CH_2CHF_2$, —$CH_2CF_3$, —$CH_2CHCl_2$, —$CH_2CCl_3$, —$CH_2CHBr_2$, and —$CH_2CBr_3$. In a still further aspect, $R^1$ is selected from hydrogen, methyl, —$CH_2F$, —$CH_2Cl$, —$CH_2Br$, —$CHF_2$, —$CF_3$, —$CHCl_2$, —$CCl_3$, —$CHBr_2$, and —$CBr_3$.

In a further aspect, $R^1$ is selected from hydrogen and C1-C8 haloalkyl. In a still further aspect, $R^1$ is selected from hydrogen and C1-C4 haloalkyl. In yet a further aspect, $R^1$ is selected from hydrogen, —$CH_2F$, —$CH_2Cl$, —$CH_2Br$, —$CH_2CH_2F$, —$CH_2CH_2Cl$, —$CH_2CH_2Br$, —$(CH_2)_2CH_2F$, —$(CH_2)_2CH_2Cl$, —$(CH_2)_2CH_2Br$, —$CHF_2$, —$CF_3$, —$CHCl_2$, —$CCl_3$, —$CHBr_2$, —$CBr_3$, —$CH_2CHF_2$, —$CH_2CF_3$, —$CH_2CHCl_2$, —$CH_2CCl_3$, —$CH_2CHBr_2$, —$CH_2CBr_3$, —$(CH_2)_2CHF_2$, —$(CH_2)_2CF_3$, —$(CH_2)_2CHCl_2$, —$(CH_2)_2CCl_3$, —$(CH_2)_2CHBr_2$, and —$(CH_2)_2CBr_3$. In an even further aspect, $R^1$ is selected from hydrogen, —$CH_2F$, —$CH_2Cl$, —$CH_2Br$, —$CH_2CH_2F$, —$CH_2CH_2Cl$, —$CH_2CH_2Br$, —$CHF_2$, —$CF_3$, —$CHCl_2$, —$CCl_3$, —$CHBr_2$, —$CBr_3$, —$CH_2CHF_2$, —$CH_2CF_3$, —$CH_2CHCl_2$, —$CH_2CCl_3$, —$CH_2CHBr_2$, and —$CH_2CBr_3$. In a still further aspect, $R^1$ is selected from hydrogen, —$CH_2F$, —$CH_2Cl$, —$CH_2Br$, —$CHF_2$, —$CF_3$, —$CHCl_2$, —$CCl_3$, —$CHBr_2$, and —$CBr_3$.

In a further aspect, $R^1$ is selected from hydrogen and C1-C8 alkyl. In a still further aspect, $R^1$ is selected from hydrogen and C1-C4 alkyl. In yet a further aspect, $R^1$ is selected from hydrogen, methyl, ethyl, n-propyl, and i-propyl. In an even further aspect, $R^1$ is selected from hydrogen, methyl, and ethyl. In a still further aspect, $R^1$ is selected from hydrogen and ethyl. In yet a further aspect, $R^1$ is selected from hydrogen and methyl.

In a further aspect, $R^1$ is C1-C8 alkyl. In a still further aspect, $R^1$ is C1-C4 alkyl. In yet a further aspect, $R^1$ is selected from methyl, ethyl, n-propyl, and i-propyl. In an even further aspect, $R^1$ is selected from methyl and ethyl. In a still further aspect, $R^1$ is ethyl. In yet a further aspect, $R^1$ is methyl.

d. $R^{2a}$, $R^{2b}$, $R^{2c}$, and $R^{2d}$ Groups

In one aspect, each of $R^{2a}$, $R^{2b}$, $R^{2c}$, and $R^{2d}$ is independently selected from hydrogen, halogen, —OH, —CN, —$NO_2$, —$NH_2$, C1-C4 alkyl, C1-C4 alkoxy, C1-C4 haloalkyl, C1-C4 alkylamino, and (C1-C4)(C1-C4) dialkylamino. In a further aspect, each of $R^{2a}$, $R^{2b}$, $R^{2c}$, and $R^{2d}$ is hydrogen.

In a further aspect, each of $R^{2a}$, $R^{2b}$, $R^{2c}$, and $R^{2d}$ is independently selected from hydrogen, —F, —Cl, —Br, —OH, —CN, —$NO_2$, —$NH_2$, methyl, ethyl, n-propyl, i-propyl, —$OCH_3$, —$OCH_2CH_3$, —$O(CH_2)_2CH_3$, —$OCH(CH_3)_2$, —$CH_2F$, —$CH_2Cl$, —$CH_2Br$, —$CH_2CH_2F$, —$CH_2CH_2Cl$, —$CH_2CH_2Br$, —$(CH_2)_2CH_2F$, —$(CH_2)_2CH_2Cl$, —$(CH_2)_2CH_2Br$, —$CHF_2$, —$CF_3$, —$CHCl_2$, —$CCl_3$, —$CHBr_2$, —$CBr_3$, —$CH_2CHF_2$, —$CH_2CF_3$, —$CH_2CHCl_2$, —$CH_2CCl_3$, —$CH_2CHBr_2$, —$CH_2CBr_3$, —$(CH_2)_2CHF_2$, —$(CH_2)_2CF_3$, —$(CH_2)_2CHCl_2$, —$(CH_2)_2CCl_3$, —$(CH_2)_2CHBr_2$, —$(CH_2)_2CBr_3$, —$NHCH_3$, —$NHCH_2CH_3$, —$NH(CH_2)_2CH_3$, —$NHCH(CH_3)_2$, —$N(CH_3)_2$, —$N(CH_2CH_3)_2$, —$N((CH_2)_2CH_3)_2$, —$N(CH(CH_3)_2)_2$, —$N(CH_3)CH_2CH_3$, —$N(CH_3)(CH_2)_2CH_3$, and —$N(CH_3)CH(CH_3)_2$. In a still further aspect, each of $R^{2a}$, $R^{2b}$, $R^{2c}$, and $R^{2d}$ is independently selected from hydrogen, —F, —Cl, —Br, —OH, —CN, —$NO_2$, —$NH_2$, methyl, ethyl, —$OCH_3$, —$OCH_2CH_3$, —$CH_2F$, —$CH_2Cl$, —$CH_2Br$, —$CH_2CH_2F$, —$CH_2CH_2Cl$, —$CH_2CH_2Br$, —$CHF_2$, —$CF_3$, —$CHCl_2$, —$CCl_3$, —$CHBr_2$, —$CBr_3$, —$CH_2CHF_2$, —$CH_2CF_3$, —$CH_2CHCl_2$, —$CH_2CCl_3$, —$CH_2CHBr_2$, —$CH_2CBr_3$, —$NHCH_3$, —$NHCH_2CH_3$, —$N(CH_3)_2$, —$N(CH_2CH_3)_2$, and —$N(CH_3)CH_2CH_3$. In yet a further aspect, each of $R^{2a}$, $R^{2b}$, $R^{2c}$, and $R^{2d}$ is independently selected from hydrogen, —F, —Cl, —Br, —OH, —CN, —$NO_2$, —$NH_2$, methyl, —$OCH_3$, —$CH_2F$, —$CH_2Cl$, —$CH_2Br$, —$CHF_2$, —$CF_3$, —$CHCl_2$, —$CCl_3$, —$CHBr_2$, —$CBr_3$, —$NHCH_3$, and —$N(CH_3)_2$.

In a further aspect, each of $R^{2a}$, $R^{2b}$, $R^{2c}$, and $R^{2d}$ is independently selected from hydrogen, halogen, C1-C4 alkyl, C1-C4 alkoxy, C1-C4 haloalkyl, C1-C4 alkylamino, and (C1-C4)(C1-C4) dialkylamino. In a still further aspect, each of $R^{2a}$, $R^{2b}$, $R^{2c}$, and $R^{2d}$ is independently selected from hydrogen, —F, —Cl, —Br, methyl, ethyl, n-propyl, i-propyl, —$OCH_3$, —$OCH_2CH_3$, —$O(CH_2)_2CH_3$, —$OCH(CH_3)_2$, —$CH_2F$, —$CH_2Cl$, —$CH_2Br$, —$CH_2CH_2F$, —$CH_2CH_2Cl$, —$CH_2CH_2Br$, —$(CH_2)_2CH_2F$, —$(CH_2)_2CH_2Cl$, —$(CH_2)_2CH_2Br$, —$CHF_2$, —$CF_3$, —$CHCl_2$, —$CCl_3$, —$CHBr_2$, —$CBr_3$, —$CH_2CHF_2$, —$CH_2CF_3$, —$CH_2CHCl_2$, —$CH_2CCl_3$, —$CH_2CHBr_2$, —$CH_2CBr_3$, —$(CH_2)_2CHF_2$, —$(CH_2)_2CF_3$, —$(CH_2)_2CHCl_2$, —$(CH_2)_2CCl_3$, —$(CH_2)_2CHBr_2$, —$(CH_2)_2$ $CBr_3$, —$NHCH_3$, —$NHCH_2CH_3$, —$NH(CH_2)_2CH_3$, —$NHCH(CH_3)_2$, —$N(CH_3)_2$, —$N(CH_2CH_3)_2$, —$N((CH_2)_2$ $CH_3)_2$, —$N(CH(CH_3)_2)_2$, —$N(CH_3)CH_2CH_3$, —$N(CH_3)(CH_2)_2CH_3$, and —$N(CH_3)CH(CH_3)_2$. In yet a further aspect, each of $R^{2a}$, $R^{2b}$, $R^{2c}$, and $R^{2d}$ is independently selected from hydrogen, —F, —Cl, —Br, methyl, ethyl, —$OCH_3$, —$OCH_2CH_3$, —$CH_2F$, —$CH_2Cl$, —$CH_2Br$, —$CH_2CH_2F$, —$CH_2CH_2Cl$, —$CH_2CH_2Br$, —$CHF_2$, —$CF_3$, —$CHCl_2$, —$CCl_3$, —$CHBr_2$, —$CBr_3$, —$CH_2CHF_2$, —$CH_2CF_3$, —$CH_2CHCl_2$, —$CH_2CCl_3$, —$CH_2CHBr_2$, —$CH_2CBr_3$, —$NHCH_3$, —$NHCH_2CH_3$, —$N(CH_3)_2$, —$N(CH_2CH_3)_2$, and —$N(CH_3)CH_2CH_3$. In an even further aspect, each of $R^{2a}$, $R^{2b}$, $R^{2c}$, and $R^{2d}$ is independently selected from hydrogen, —F, —Cl, —Br, methyl, —$OCH_3$, —$CH_2F$, —$CH_2Cl$, —$CH_2Br$, —$CHF_2$, —$CF_3$, —$CHCl_2$, —$CCl_3$, —$CHBr_2$, —$CBr_3$, —$NHCH_3$, and —$N(CH_3)_2$.

In a further aspect, each of $R^{2a}$, $R^{2b}$, $R^{2c}$, and $R^{2d}$ is independently selected from hydrogen and halogen. In a still further aspect, each of $R^{2a}$, $R^{2b}$, $R^{2c}$, and $R^{2d}$ is independently selected from hydrogen, —F, —Cl, and —Br. In yet a further aspect, each of $R^{2a}$, $R^{2b}$, $R^{2c}$, and $R^{2d}$ is independently selected from hydrogen, —F, and —Cl. In an even further aspect, each of $R^{2a}$, $R^{2b}$, $R^{2c}$, and $R^{2d}$ is independently selected from hydrogen and —Cl. In a still further aspect, each of $R^{2a}$, $R^{2b}$, $R^{2c}$, and $R^{2d}$ is independently selected from hydrogen and —F.

In a further aspect, each of $R^{2a}$, $R^{2b}$, $R^{2c}$, and $R^{2d}$ is independently selected from hydrogen and C1-C4 alkyl. In a still further aspect, each of $R^{2a}$, $R^{2b}$, $R^{2c}$, and $R^{2d}$ is independently selected from hydrogen, methyl, ethyl, n-propyl, and i-propyl. In yet a further aspect, each of $R^{2a}$, $R^{2b}$, $R^{2c}$, and $R^{2d}$ is independently selected from hydrogen, methyl, and ethyl. In an even further aspect, each of $R^{2a}$, $R^{2b}$, $R^{2c}$, and $R^{2d}$ is independently selected from hydrogen and ethyl. In a still further aspect, each of $R^{2a}$, $R^{2b}$, $R^{2c}$, and $R^{2d}$ is independently selected from hydrogen and methyl.

e. $R^3$ Groups

In one aspect, $R^3$, when present, is selected from hydrogen and C1-C8 alkyl. In a further aspect, $R^3$, when present, is selected from hydrogen and C1-C4 alkyl. In a still further aspect, $R^3$, when present, is hydrogen.

In a further aspect, $R^3$, when present, is selected from methyl, ethyl, n-propyl, i-propyl, n-butyl, i-butyl, s-butyl, and t-butyl. In a still further aspect, $R^3$, when present, is selected from methyl, ethyl, n-propyl, and i-propyl. In yet a further aspect, $R^3$, when present, is selected from methyl and ethyl. In an even further aspect, $R^3$, when present, is ethyl. In a still further aspect, $R^3$, when present, is methyl.

f. $R^4$ Groups

In one aspect, $R^4$, when present, is selected from hydrogen and C1-C8 alkyl. In a further aspect, $R^4$, when present, is selected from hydrogen and C1-C4 alkyl. In a still further aspect, $R^4$, when present, is hydrogen.

In a further aspect, $R^4$, when present, is selected from methyl, ethyl, n-propyl, i-propyl, n-butyl, i-butyl, s-butyl, and t-butyl. In a still further aspect, $R^4$, when present, is selected from methyl, ethyl, n-propyl, and i-propyl. In yet a further aspect, $R^4$, when present, is selected from methyl and ethyl. In an even further aspect, $R^4$, when present, is ethyl. In a still further aspect, $R^4$, when present, is methyl.

g. $R^{5a}$ and $R^{5b}$ Groups

In one aspect, each of $R^{5a}$ and $R^{5b}$, when present, is independently selected from hydrogen and C1-C4 alkyl. In a further aspect, each of $R^{5a}$ and $R^{5b}$, when present, is hydrogen.

In a further aspect, each of $R^{5a}$ and $R^{5b}$, when present, is independently selected from hydrogen, methyl, ethyl, n-propyl, and i-propyl. In a still further aspect, each of $R^{5a}$ and $R^{5b}$, when present, is independently selected from hydrogen, methyl, and ethyl. In yet a further aspect, each of $R^{5a}$ and $R^{5b}$, when present, is independently selected from hydrogen and ethyl. In an even further aspect, each of $R^{5a}$ and $R^{5b}$, when present, is independently selected from hydrogen and methyl.

In a further aspect, each of $R^{5a}$ and $R^{5b}$, when present, is independently selected from methyl, ethyl, n-propyl, i-propyl, n-butyl, i-butyl, s-butyl, and t-butyl. In a still further aspect, each of $R^{5a}$ and $R^{5b}$, when present, is independently selected from methyl, ethyl, n-propyl, and i-propyl. In yet a further aspect, each of $R^{5a}$ and $R^{5b}$, when present, is independently selected from methyl and ethyl. In an even further aspect, each of $R^{5a}$ and $R^{5b}$, when present, is ethyl. In a still further aspect, each of $R^{5a}$ and $R^{5b}$, when present, is methyl.

h. $R^6$ Groups

In one aspect, $R^6$, when present, is selected from hydrogen and C1-C4 alkyl. In a further aspect, $R^6$, when present, is hydrogen.

In a further aspect, $R^6$, when present, is selected from hydrogen, methyl, ethyl, n-propyl, and i-propyl. In a still further aspect, $R^6$, when present, is selected from hydrogen, methyl, and ethyl. In yet a further aspect, $R^6$, when present, is selected from hydrogen and ethyl. In an even further aspect, $R^6$, when present, is selected from hydrogen and methyl.

In a further aspect, $R^6$, when present, is selected from methyl, ethyl, n-propyl, i-propyl, n-butyl, i-butyl, s-butyl, and t-butyl. In a still further aspect, $R^6$, when present, is from methyl, ethyl, n-propyl, and i-propyl. In yet a further aspect, $R^6$, when present, is from methyl and ethyl. In an even further aspect, $R^6$, when present, is ethyl. In a still further aspect, $R^6$, when present, is methyl.

i. $Ar^1$ Groups

In one aspect, $Ar^1$ is selected from aryl and heteroaryl and substituted with 0, 1, or 2 groups independently selected from halogen, —OH, —CN, —$NO_2$, —$NH_2$, C1-C4 alkyl, C1-C4 alkoxy, C1-C4 haloalkyl, C1-C4 alkylamino, and (C1-C4)(C1-C4) dialkylamino. In a further aspect, $Ar^1$ is selected from aryl and heteroaryl and substituted with 0 or 1 group selected from halogen, —OH, —CN, —$NO_2$, —$NH_2$, C1-C4 alkyl, C1-C4 alkoxy, C1-C4 haloalkyl, C1-C4 alkylamino, and (C1-C4)(C1-C4) dialkylamino. In a still further aspect, $Ar^1$ is selected from aryl and heteroaryl and monosubstituted with a group selected from halogen, —OH, —CN, —$NO_2$, —$NH_2$, C1-C4 alkyl, C1-C4 alkoxy, C1-C4 haloalkyl, C1-C4 alkylamino, and (C1-C4)(C1-C4) dialkylamino. In yet a further aspect, $Ar^1$ is selected from aryl and heteroaryl and unsubstituted.

In a further aspect, $Ar^1$ is aryl substituted with 0, 1, or 2 groups independently selected from halogen, —OH, —CN, —$NO_2$, —$NH_2$, C1-C4 alkyl, C1-C4 alkoxy, C1-C4 haloalkyl, C1-C4 alkylamino, and (C1-C4)(C1-C4) dialkylamino. In a still further aspect, $Ar^1$ is aryl substituted with 0 or 1 group selected from halogen, —OH, —CN, —$NO_2$, —$NH_2$, C1-C4 alkyl, C1-C4 alkoxy, C1-C4 haloalkyl, C1-C4 alkylamino, and (C1-C4)(C1-C4) dialkylamino. In yet a further aspect, $Ar^1$ is aryl monosubstituted with a group selected from halogen, —OH, —CN, —$NO_2$, —$NH_2$, C1-C4 alkyl, C1-C4 alkoxy, C1-C4 haloalkyl, C1-C4 alkylamino, and (C1-C4)(C1-C4) dialkylamino. In an even further aspect, $Ar^1$ is unsubstituted aryl.

In a further aspect, $Ar^1$ is phenyl substituted with 0, 1, or 2 groups independently selected from halogen, —OH, —CN, —$NO_2$, —$NH_2$, C1-C4 alkyl, C1-C4 alkoxy, C1-C4 haloalkyl, C1-C4 alkylamino, and (C1-C4)(C1-C4) dialkylamino. In a still further aspect, $Ar^1$ is phenyl substituted with 0 or 1 group selected from halogen, —OH, —CN, —$NO_2$, —$NH_2$, C1-C4 alkyl, C1-C4 alkoxy, C1-C4 haloalkyl, C1-C4 alkylamino, and (C1-C4)(C1-C4) dialkylamino. In yet a further aspect, $Ar^1$ is phenyl monosubstituted with a group selected from halogen, —OH, —CN, —$NO_2$, —$NH_2$, C1-C4 alkyl, C1-C4 alkoxy, C1-C4 haloalkyl, C1-C4 alkylamino, and (C1-C4)(C1-C4) dialkylamino. In an even further aspect, $Ar^1$ is unsubstituted phenyl.

In a further aspect, $Ar^1$ is heteroaryl substituted with 0, 1, or 2 groups independently selected from halogen, —OH, —CN, —$NO_2$, —$NH_2$, C1-C4 alkyl, C1-C4 alkoxy, C1-C4 haloalkyl, C1-C4 alkylamino, and (C1-C4)(C1-C4) dialkylamino. In a still further aspect, $Ar^1$ is heteroaryl substituted with 0 or 1 group selected from halogen, —OH, —CN, —$NO_2$, —$NH_2$, C1-C4 alkyl, C1-C4 alkoxy, C1-C4 haloalkyl, C1-C4 alkylamino, and (C1-C4)(C1-C4) dialkylamino. In yet a further aspect, $Ar^1$ is heteroaryl monosubstituted with a group selected from halogen, —OH, —CN, —$NO_2$, —$NH_2$, C1-C4 alkyl, C1-C4 alkoxy, C1-C4 haloalkyl, C1-C4 alkylamino, and (C1-C4)(C1-C4) dialkylamino. In an even further aspect, $Ar^1$ is unsubstituted heteroaryl.

In a further aspect, $Ar^1$ is selected from triazolyl, imidazolyl, pyrazolyl, pyrrolyl, benzothiophenyl, benzofuranyl, furanyl, thiophenyl, pyridinyl, pyrimidinyl, indolyl, quinolinyl, isoquinolinyl, and purinyl and substituted with 0, 1, or 2 groups independently selected from halogen, —OH, —CN, —$NO_2$, —$NH_2$, C1-C4 alkyl, C1-C4 alkoxy, C1-C4 haloalkyl, C1-C4 alkylamino, and (C1-C4)(C1-C4) dialkylamino. In a still further aspect, $Ar^1$ is selected from triazolyl, imidazolyl, pyrazolyl, pyrrolyl, benzothiophenyl, benzofuranyl, furanyl, thiophenyl, pyridinyl, pyrimidinyl, indolyl, quinolinyl, isoquinolinyl, and purinyl and substituted with 0 or 1 group selected from halogen, —OH, —CN, —$NO_2$, —$NH_2$, C1-C4 alkyl, C1-C4 alkoxy, C1-C4 haloalkyl, C1-C4 alkylamino, and (C1-C4)(C1-C4) dialkylamino. In yet a further aspect, $Ar^1$ is selected from triazolyl, imidazolyl, pyrazolyl, pyrrolyl, benzothiophenyl, benzofuranyl, furanyl, thiophenyl, pyridinyl, pyrimidinyl, indolyl, quinolinyl, isoquinolinyl, and purinyl and monosubstituted with a group selected from halogen, —OH, —CN, —$NO_2$, —$NH_2$, C1-C4 alkyl, C1-C4 alkoxy, C1-C4 haloalkyl, C1-C4 alkylamino, and (C1-C4)(C1-C4) dialkylamino. In an even further aspect, $Ar^1$ is selected from triazolyl, imidazolyl, pyrazolyl, pyrrolyl, benzothiophenyl, benzofuranyl, furanyl, thiophenyl, pyridinyl, pyrimidinyl, indolyl, quinolinyl, isoquinolinyl, and purinyl and unsubstituted.

j. $Ar^2$ Groups

In one aspect, $Ar^2$ is selected from aryl and heteroaryl and substituted with 0, 1, or 2 groups independently selected from halogen, —OH, —CN, —$NO_2$, —$NH_2$, C1-C4 alkyl, C1-C4 alkoxy, C1-C4 haloalkyl, C1-C4 alkylamino, and (C1-C4)(C1-C4) dialkylamino. In a further aspect, $Ar^2$ is selected from aryl and heteroaryl and substituted with 0 or 1 group selected from halogen, —OH, —CN, —$NO_2$, —$NH_2$, C1-C4 alkyl, C1-C4 alkoxy, C1-C4 haloalkyl, C1-C4 alkylamino, and (C1-C4)(C1-C4) dialkylamino. In a still further aspect, $Ar^2$ is selected from aryl and heteroaryl and monosubstituted with a group selected from halogen, —OH, —CN, —$NO_2$, —$NH_2$, C1-C4 alkyl, C1-C4 alkoxy, C1-C4 haloalkyl, C1-C4 alkylamino, and (C1-C4)(C1-C4) dialkylamino. In yet a further aspect, $Ar^2$ is selected from aryl and heteroaryl and unsubstituted.

In a further aspect, $Ar^2$ is aryl substituted with 0, 1, or 2 groups independently selected from halogen, —OH, —CN, —$NO_2$, —$NH_2$, C1-C4 alkyl, C1-C4 alkoxy, C1-C4 haloalkyl, C1-C4 alkylamino, and (C1-C4)(C1-C4) dialkylamino. In a still further aspect, $Ar^2$ is aryl substituted with 0 or 1 group selected from halogen, —OH, —CN, —$NO_2$, —$NH_2$, C1-C4 alkyl, C1-C4 alkoxy, C1-C4 haloalkyl, C1-C4 alkylamino, and (C1-C4)(C1-C4) dialkylamino. In yet a further aspect, $Ar^2$ is aryl monosubstituted with a group selected from halogen, —OH, —CN, —$NO_2$, —$NH_2$, C1-C4 alkyl, C1-C4 alkoxy, C1-C4 haloalkyl, C1-C4 alkylamino, and (C1-C4)(C1-C4) dialkylamino. In an even further aspect, $Ar^2$ is unsubstituted aryl.

In a further aspect, $Ar^2$ is phenyl substituted with 0, 1, or 2 groups independently selected from halogen, —OH, —CN, —$NO_2$, —$NH_2$, C1-C4 alkyl, C1-C4 alkoxy, C1-C4 haloalkyl, C1-C4 alkylamino, and (C1-C4)(C1-C4) dialkylamino. In a still further aspect, $Ar^2$ is phenyl substituted with 0 or 1 group selected from halogen, —OH, —CN, —$NO_2$, —$NH_2$, C1-C4 alkyl, C1-C4 alkoxy, C1-C4 haloalkyl, C1-C4 alkylamino, and (C1-C4)(C1-C4) dialkylamino. In yet a further aspect, $Ar^2$ is phenyl monosubstituted with a group selected from halogen, —OH, —CN, —$NO_2$, —$NH_2$, C1-C4 alkyl, C1-C4 alkoxy, C1-C4 haloalkyl, C1-C4 alkylamino, and (C1-C4)(C1-C4) dialkylamino. In an even further aspect, $Ar^2$ is unsubstituted phenyl.

In a further aspect, $Ar^2$ is heteroaryl substituted with 0, 1, or 2 groups independently selected from halogen, —OH, —CN, —$NO_2$, —$NH_2$, C1-C4 alkyl, C1-C4 alkoxy, C1-C4 haloalkyl, C1-C4 alkylamino, and (C1-C4)(C1-C4) dialkylamino. In a still further aspect, $Ar^2$ is heteroaryl substituted with 0 or 1 group selected from halogen, —OH, —CN, —$NO_2$, —$NH_2$, C1-C4 alkyl, C1-C4 alkoxy, C1-C4 haloalkyl, C1-C4 alkylamino, and (C1-C4)(C1-C4) dialkylamino. In yet a further aspect, $Ar^2$ is heteroaryl monosubstituted with a group selected from halogen, —OH, —CN, —$NO_2$, —$NH_2$, C1-C4 alkyl, C1-C4 alkoxy, C1-C4 haloalkyl, C1-C4 alkylamino, and (C1-C4)(C1-C4) dialkylamino. In an even further aspect. $Ar^2$ is unsubstituted heteroaryl.

In a further aspect, $Ar^2$ is selected from triazolyl, imidazolyl, pyrazolyl, pyrrolyl, benzothiophenyl, benzofuranyl, furanyl, thiophenyl, pyridinyl, pyrimidinyl, indolyl, quinolinyl, isoquinolinyl, and purinyl and substituted with 0, 1, or 2 groups independently selected from halogen, —OH, —CN, —$NO_2$, —$NH_2$, C1-C4 alkyl, C1-C4 alkoxy, C1-C4 haloalkyl, C1-C4 alkylamino, and (C1-C4)(C1-C4) dialkylamino. In a still further aspect, $Ar^2$ is selected from triazolyl, imidazolyl, pyrazolyl, pyrrolyl, benzothiophenyl, benzofuranyl, furanyl, thiophenyl, pyridinyl, pyrimidinyl, indolyl, quinolinyl, isoquinolinyl, and purinyl and substituted with 0 or 1 group selected from halogen, —OH, —CN, —$NO_2$, —$NH_2$, C1-C4 alkyl, C1-C4 alkoxy, C1-C4 haloalkyl, C1-C4 alkylamino, and (C1-C4)(C1-C4) dialkylamino. In yet a further aspect, $Ar^2$ is selected from triazolyl, imidazolyl, pyrazolyl, pyrrolyl, benzothiophenyl, benzofuranyl, furanyl, thiophenyl, pyridinyl, pyrimidinyl, indolyl, quinolinyl, isoquinolinyl, and purinyl and and monosubstituted with a group selected from halogen, —OH, —CN, —$NO_2$, —$NH_2$, C1-C4 alkyl, C1-C4 alkoxy, C1-C4 haloalkyl, C1-C4 alkylamino, and (C1-C4)(C1-C4) dialkylamino. In an even further aspect, $Ar^2$ is selected from triazolyl, imidazolyl, pyrazolyl, pyrrolyl, benzothiophenyl, benzofuranyl, furanyl, thiophenyl, pyridinyl, pyrimidinyl, indolyl, quinolinyl, isoquinolinyl, and purinyl and unsubstituted.

k. $Cy^1$ Groups

In one aspect, $Cy^1$ is selected from C3-C7 cycloalkyl and C2-C7 heterocycloalkyl and substituted with 0, 1, or 2 groups independently selected from halogen, —OH, —CN, —$NO_2$, —$NH_2$, C1-C4 alkyl, C1-C4 alkoxy, C1-C4 haloalkyl, C1-C4 alkylamino, and (C1-C4)(C1-C4) dialkylamino. In a further aspect, $Cy^1$ is selected from C3-C7 cycloalkyl and C2-C7 heterocycloalkyl and substituted with 0 or 1 group selected from halogen, —OH, —CN, —$NO_2$, —$NH_2$, C1-C4 alkyl, C1-C4 alkoxy, C1-C4 haloalkyl, C1-C4 alkylamino, and (C1-C4)(C1-C4) dialkylamino. In a still further aspect, $Cy^1$ is selected from C3-C7 cycloalkyl and C2-C7 heterocycloalkyl and monosubstituted with a group selected from halogen, —OH, —CN, —$NO_2$, —$NH_2$, C1-C4 alkyl, C1-C4 alkoxy, C1-C4 haloalkyl, C1-C4 alkylamino, and (C1-C4)(C1-C4) dialkylamino. In yet a further aspect, $Cy^1$ is selected from C3-C7 cycloalkyl and C2-C7 heterocycloalkyl and unsubstituted.

In a further aspect, $Cy^1$ is C3-C7 cycloalkyl substituted with 0, 1, or 2 groups independently selected from halogen, —OH, —CN, —$NO_2$, —$NH_2$, C1-C4 alkyl, C1-C4 alkoxy, C1-C4 haloalkyl, C1-C4 alkylamino, and (C1-C4)(C1-C4) dialkylamino. In a still further aspect, $Cy^1$ is C3-C7 cycloalkyl substituted with 0 or 1 group selected from halogen, —OH, —CN, —$NO_2$, —$NH_2$, C1-C4 alkyl, C1-C4 alkoxy, C1-C4 haloalkyl, C1-C4 alkylamino, and (C1-C4)(C1-C4) dialkylamino. In yet a further aspect, $Cy^1$ is C3-C7 cycloalkyl monosubstituted with a group selected from halogen, —OH, —CN, —$NO_2$, —$NH_2$, C1-C4 alkyl, C1-C4 alkoxy, C1-C4 haloalkyl, C1-C4 alkylamino, and (C1-C4)(C1-C4) dialkylamino. In an even further aspect, $Cy^1$ is unsubstituted C3-C7 cycloalkyl.

In a further aspect, $Cy^1$ is selected from cyclopropyl, cyclopentyl, and cyclohexyl and substituted with 0, 1, or 2 groups independently selected from halogen, —OH, —CN, —$NO_2$, —$NH_2$, C1-C4 alkyl, C1-C4 alkoxy, C1-C4 haloalkyl, C1-C4 alkylamino, and (C1-C4)(C1-C4) dialkylamino. In a still further aspect, $Cy^1$ is selected from cyclopropyl, cyclopentyl, and cyclohexyl and substituted with 0 or 1 group selected from halogen, —OH, —CN, —$NO_2$, —$NH_2$, C1-C4 alkyl, C1-C4 alkoxy, C1-C4 haloalkyl, C1-C4 alkylamino, and (C1-C4)(C1-C4) dialkylamino. In yet a further aspect, $Cy^1$ is selected from cyclopropyl, cyclopentyl, and cyclohexyl and monosubstituted with a group selected from halogen, —OH, —CN, —$NO_2$, —$NH_2$, C1-C4 alkyl, C1-C4 alkoxy, C1-C4 haloalkyl, C1-C4 alkylamino, and (C1-C4)(C1-C4) dialkylamino. In an even further aspect, $Cy^1$ is selected from cyclopropyl, cyclopentyl, and cyclohexyl and unsubstituted.

In a further aspect, $Cy^1$ is C2-C7 heterocycloalkyl substituted with 0, 1, or 2 groups independently selected from halogen, —OH, —CN, —$NO_2$, —$NH_2$, C1-C4 alkyl, C1-C4 alkoxy, C1-C4 haloalkyl, C1-C4 alkylamino, and (C1-C4)(C1-C4) dialkylamino. In a still further aspect, $Cy^1$ is C2-C7 heterocycloalkyl substituted with 0 or 1 group selected from halogen, —OH, —CN, —$NO_2$, —$NH_2$, C1-C4 alkyl, C1-C4 alkoxy, C1-C4 haloalkyl, C1-C4 alkylamino, and (C1-C4)(C1-C4) dialkylamino. In yet a further aspect, $Cy^1$ is C2-C7 heterocycloalkyl monosubstituted with a group selected from halogen, —OH, —CN, —$NO_2$, —$NH_2$, C1-C4 alkyl, C1-C4 alkoxy, C1-C4 haloalkyl, C1-C4 alkylamino, and (C1-C4)(C1-C4) dialkylamino. In an even further aspect, $Cy^1$ is unsubstituted C2-C7 heterocycloalkyl.

In a further aspect, $Cy^1$ is selected from pyrrolidinyl, tetrahydrothiophenyl, furanyl, piperidinyl, and tetrahydropyranyl and substituted with 0, 1, or 2 groups independently selected from halogen, —OH, —CN, —$NO_2$, —$NH_2$, C1-C4 alkyl, C1-C4 alkoxy, C1-C4 haloalkyl, C1-C4 alkylamino, and (C1-C4)(C1-C4) dialkylamino. In a still further aspect, $Cy^1$ is selected from pyrrolidinyl, tetrahydrothiophenyl, furanyl, piperidinyl, and tetrahydropyranyl and substituted with 0 or 1 group selected from halogen, —OH, —CN, —$NO_2$, —$NH_2$, C1-C4 alkyl, C1-C4 alkoxy, C1-C4 haloalkyl, C1-C4 alkylamino, and (C1-C4)(C1-C4) dialkylamino. In yet a further aspect, $Cy^1$ is selected from pyrrolidinyl, tetrahydrothiophenyl, furanyl, piperidinyl, and tetrahydropyranyl and monosubstituted with a group selected from halogen, —OH, —CN, —$NO_2$, —$NH_2$, C1-C4 alkyl, C1-C4 alkoxy, C1-C4 haloalkyl, C1-C4 alkylamino, and (C1-C4)(C1-C4) dialkylamino. In an even further aspect, $Cy^1$ is selected from pyrrolidinyl, tetrahydrothiophenyl, furanyl, piperidinyl, and tetrahydropyranyl and unsubstituted.

2. Example Compounds

In one aspect, a compound can be present as one or more of the following structures:

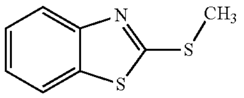

and

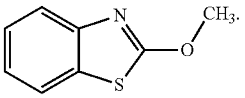

3. Prophetic Compound Examples

The following compound examples are prophetic, and can be prepared using the synthesis methods described herein above and other general methods as needed as would be known to one skilled in the art. It is anticipated that the prophetic compounds would be active as inhibitors of germination of *C. perfringens* spores, and such activity can be determined using the assay methods described herein.

In one aspect, a compound can be selected from:

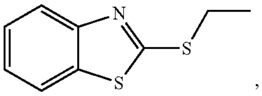

,

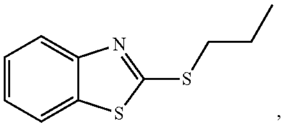

,

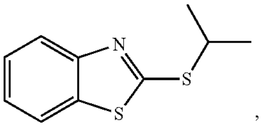

,

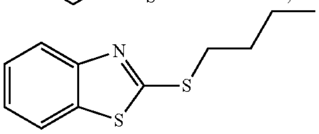

,

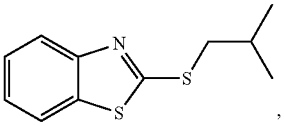

,

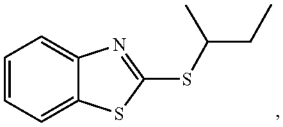

,

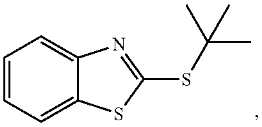

,

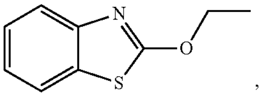

,

-continued
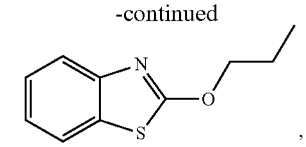
,
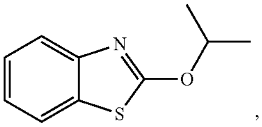
,
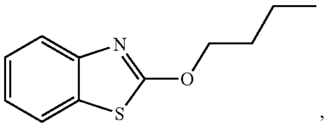
,
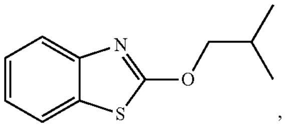
,
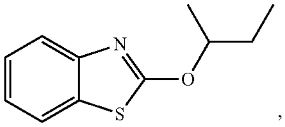
,
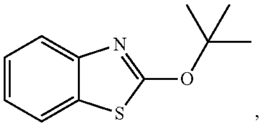
,
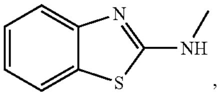
,
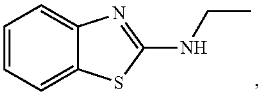
,
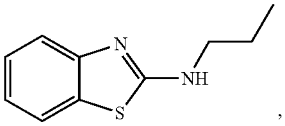
,
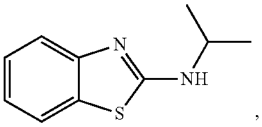
,
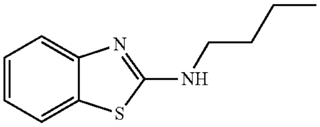
,
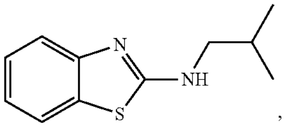
,
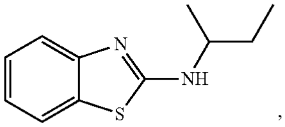
,
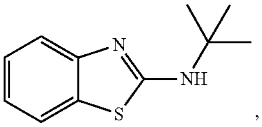
,
-continued
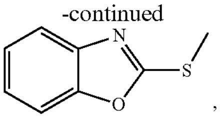
,
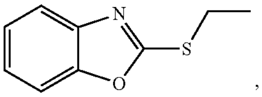
,
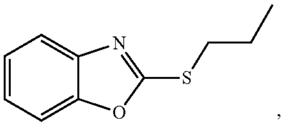
,
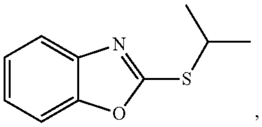
,
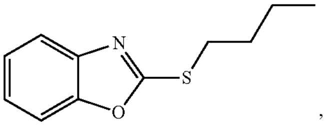
,
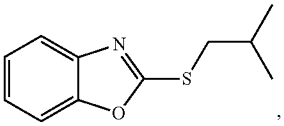
,
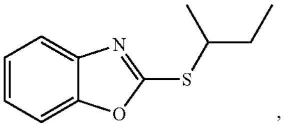
,
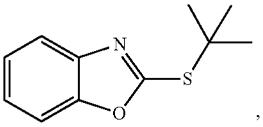
,
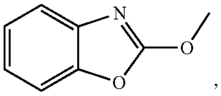
,
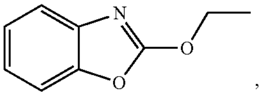
,
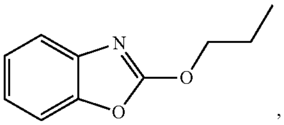
,
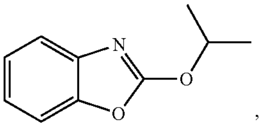
,
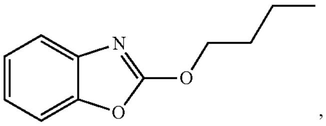
,
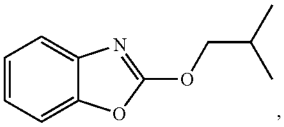
, -continued

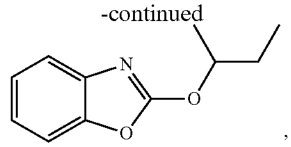
,
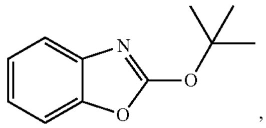
,
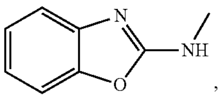
,
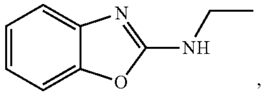
,
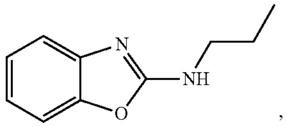
,
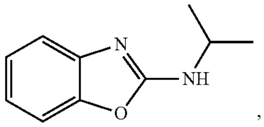
,
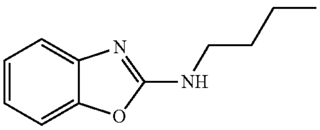
,
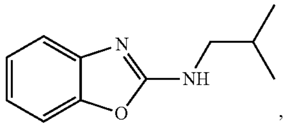
,
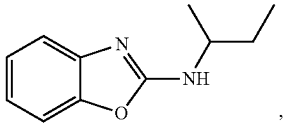
,
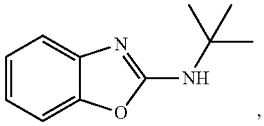
,
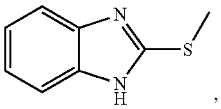
,
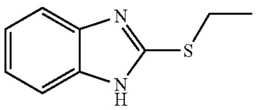
,
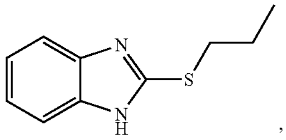
,
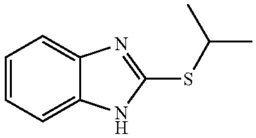
, and -continued

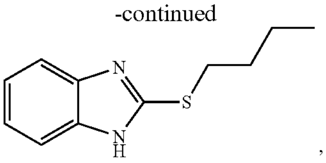
, or a pharmaceutically acceptable salt thereof.

C. *C. Perfringens*

The first step in *C. perfringens* pathogenesis is the germination of ingested spores into replicating bacteria in the gut of hosts. Thus, as described herein, it is possible that compounds able to curtail *C. perfringens* spore germination will also prevent NE. For example, anti-germinants may be added as supplements to the feed of farmed fowl (e.g., chickens, turkeys, geese, and ducks), as well as to the feed of other farm animals such as cattle, sheep, horses, and pigs, for example. Anti-germinants have the advantage that replicating bacteria will not be under selective pressure, thus reducing the possibility of resistance development. Further, since NE is an extracellular, intestinal infection, compounds need only to be optimized for retention in the gastrointestinal tract.

D. Feed Compositions

Compounds for use as described herein can be incorporated into compositions for experimental use or for administration to fowl that may experience adverse effects (e.g., NE) from exposure to germinated *C. perfringens*. A composition can include, for example, one or more heteroaromatic compounds (e.g., 2-MOB or 2-MTB, an analog thereof, or a pharmaceutically acceptable salt thereof) as described herein, in combination with a carrier.

Thus, disclosed are feed compositions comprising feed components and a compound having a structure represented by a formula:

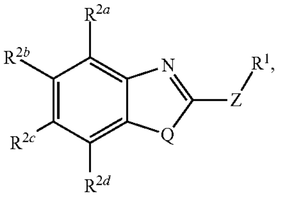

wherein Q is selected from O, S, and $NR^3$; wherein $R^3$, when present, is selected from hydrogen and C1-C8 alkyl; wherein Z is selected from O, S, and $NR^4$; wherein $R^4$, when present, is selected from hydrogen and C1-C8 alkyl; wherein $R^1$ is selected from hydrogen, C1-C8 alkyl, C1-C8 haloalkyl, $—CR^{5a}R^{5b}(C{=}O)NHN{=}CR^6Ar^1$, $Cy^1$, and $Ar^2$, provided that if Q is $NR^3$ then $R^1$ is not $—CR^{5a}R^{5b}(C{=}O)R^5$; wherein each of $R^{5a}$ and $R^{5b}$, when present, is independently selected from hydrogen and C1-C4 alkyl; wherein $R^6$, when present, is selected from hydrogen and C1-C4 alkyl; wherein $Cy^1$ is selected from C3-C7 cycloalkyl and C2-C7 heterocycloalkyl and substituted with 0, 1, or 2 groups independently selected from halogen, —OH, —CN, $—NO_2$, $—NH_2$, C1-C4 alkyl, C1-C4 alkoxy, C1-C4 haloalkyl, C1-C4 alkylamino, and (C1-C4)(C1-C4) dialkylamino; wherein $Ar^1$ is selected from aryl and heteroaryl and substituted with 0, 1, or 2 groups independently selected from halogen, —OH, —CN, —$NO_2$, —$NH_2$, C1-C4 alkyl, C1-C4 alkoxy, C1-C4 haloalkyl, C1-C4 alkylamino, and (C1-C4)(C1-C4) dialkylamino; wherein $Ar^2$ is selected from aryl and heteroaryl and substituted with 0, 1, or 2 groups independently selected from halogen, —OH, —CN, —$NO_2$, —$NH_2$, C1-C4 alkyl, C1-C4 alkoxy, C1-C4 haloalkyl, C1-C4 alkylamino, and (C1-C4)(C1-C4) dialkylamino; and wherein each of $R^{2a}$, $R^{2b}$, $R^{2c}$, and $R^{2d}$ is independently selected from hydrogen, halogen, —OH, —CN, —$NO_2$, —$NH_2$, C1-C4 alkyl, C1-C4 alkoxy, C1-C4 haloalkyl, C1-C4 alkylamino, and (C1-C4)(C1-C4) dialkylamino.

Suitable concentrations of a compound within a composition can range from, for example, about 0.1 nM to about 100 mM (e.g., about 0.1 nM to about 1 nM, about 1 nM to about 10 nM, about 10 nM to about 0.1 mM, about 0.1 mM to about 0.5 mM, about 0.5 mM to about 1 mM, about 1 mM to about 5 mM, about 5 mM to about 10 mM, about 10 mM to about 25 mM, about 25 mM to about 50 mM, about 50 mM to about 75 mM, or about 75 mM to about 100 mM).

Suitable carriers can include, without limitation, solvents, suspending agents, stabilizing agents, or any other vehicle for delivering one or more compounds to a recipient. Suitable carriers typically are nontoxic to the organism being exposed thereto at the dosages and concentrations employed. Carriers can be liquid or solid, and can be selected with the planned manner of administration in mind so as to provide for the desired bulk, consistency, and other pertinent transport and chemical properties, when combined with one or more compounds and any other components of a given composition. Suitable carriers can include, by way of example and not limitation, water, saline solution, binding agents (e.g., polyvinylpyrrolidone or hydroxypropyl methylcellulose), fillers (e.g., lactose and other sugars, gelatin, or calcium sulfate), lubricants (e.g., starch, polyethylene glycol, or sodium acetate), disintegrates (e.g., starch or sodium starch glycolate), and wetting agents (e.g., sodium lauryl sulfate). Useful carriers also can include aqueous pH buffered solutions or liposomes, as well as buffers such as phosphate, citrate, and other organic acids, antioxidants such as ascorbic acid, low molecular weight (less than about 10 residues) polypeptides, proteins such as serum albumin, gelatin, or immunoglobulins, hydrophilic polymers such as polyvinylpyrrolidone, amino acids such as glycine, glutamine, asparagine, arginine or lysine, monosaccharides, disaccharides, and other carbohydrates including glucose, mannose or dextrins, chelating agents such as EDTA, sugar alcohols such as mannitol or sorbitol, salt-forming counterions such as sodium, and/or nonionic surfactants such as TWEEN™, polyethylene glycol (PEG), and PLURONICS™.

Compositions can be formulated by mixing one or more compounds as described herein with one or more carriers, diluents, and/or adjuvants, and optionally other agents that can be incorporated into formulations to provide improved transfer, delivery, tolerance, and the like. Compositions can be formulated, e.g., in lyophilized formulations, aqueous solutions, dispersions, or solid preparations, such as tablets, dragees, or capsules. Pharmaceutical compositions can include, without limitation, solutions, emulsions, aqueous suspensions, and liposome-containing formulations. These compositions can be generated from a variety of components that include, for example, preformed liquids, self-emulsifying solids and self-emulsifying semisolids. Emulsions are often biphasic systems comprising of two immiscible liquid phases intimately mixed and dispersed with each other; in general, emulsions are either of the water-in-oil (w/o) or oil-in-water (o/w) variety. Emulsion formulations have been widely used for oral delivery of therapeutics due to their ease of formulation and efficacy of solubilization, absorption, and bioavailability.

Since *C. perfringens* is an extracellular organism found in the gut, the compounds and compositions provided herein can be optimized for retention in the gastrointestinal tract. Such optimization can include, for example, adding hydrophobic groups to the structure, or encapsulating the compound in gelatin or other appropriate media.

In some embodiments, a compound as described herein can be combined with feed (e.g., poultry feed), such that the compound is ingested as the birds eat. Thus, this document provides feed containing (e.g., mixed with or coated with) a compound that reduces or prevents germination of *C. perfringens*, where the compound is a heteroaromatic compound (e.g., 2-MOB or 2-MTB, or an analog thereof) as described herein. Suitable varieties of feed include those that are commercially available, for example.

E. Methods of Making the Compounds

In various aspects, the inventions relates to methods of making compounds useful to prevent diseases associated with infections caused by *C. perfringens*. Thus, in one aspect, disclosed are methods of making compounds having a structure represented by a formula:

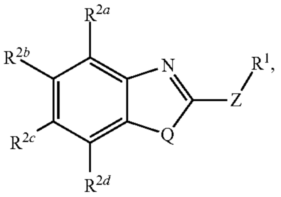

wherein Q is selected from O, S, and $NR^3$; wherein $R^3$, when present, is selected from hydrogen and C1-C8 alkyl; wherein Z is selected from O, S, and $NR^4$; wherein $R^4$, when present, is selected from hydrogen and C1-C8 alkyl; wherein $R^1$ is selected from hydrogen, C1-C8 alkyl, C1-C8 haloalkyl, —$CR^{5a}R^{5b}$(C═O)NHN═$CR^6Ar^1$, $Cy^1$, and $Ar^2$, provided that if Q is $NR^3$ then $R^1$ is not —$CR^{5a}R^{5b}$(C═O)$R^5$; wherein each of $R^{5a}$ and $R^{5b}$, when present, is independently selected from hydrogen and C1-C4 alkyl; wherein $R^6$, when present, is selected from hydrogen and C1-C4 alkyl; wherein $Cy^1$ is selected from C3-C7 cycloalkyl and C2-C7 heterocycloalkyl and substituted with 0, 1, or 2 groups independently selected from halogen, —OH, —CN, —$NO_2$, —$NH_2$, C1-C4 alkyl, C1-C4 alkoxy, C1-C4 haloalkyl, C1-C4 alkylamino, and (C1-C4)(C1-C4) dialkylamino; wherein $Ar^1$ is selected from aryl and heteroaryl and substituted with 0, 1, or 2 groups independently selected from halogen, —OH, —CN, —$NO_2$, —$NH_2$, C1-C4 alkyl, C1-C4 alkoxy, C1-C4 haloalkyl, C1-C4 alkylamino, and (C1-C4)(C1-C4) dialkylamino; wherein $Ar^2$ is selected from aryl and heteroaryl and substituted with 0, 1, or 2 groups independently selected from halogen, —OH, —CN, —$NO_2$, —$NH_2$, C1-C4 alkyl, C1-C4 alkoxy, C1-C4 haloalkyl, C1-C4 alkylamino, and (C1-C4)(C1-C4) dialkylamino; and wherein each of $R^{2a}$, $R^{2b}$, $R^{2c}$, and $R^{2d}$ is independently selected from hydrogen, halogen, —OH, —CN, —$NO_2$, —$NH_2$, C1-C4 alkyl, C1-C4 alkoxy, C1-C4 haloalkyl, C1-C4 alkylamino, and (C1-C4)(C1-C4) dialkylamino.

In various aspects, procedures known in the art (e.g., methods described by Seijas et al. in, for example, *Synlett,* 2007, 313-316) can be used to synthesize benzoazole analogs. For example, various alkyl and aryl carboxylic acids can be individually aliquoted into multi-well plates, and each well can be supplemented with o-aminophenol and Lawesson's reagent. The mixture can be irradiated in a microwave oven, and crude mixtures can be purified in parallel by recrystallization and/or flash chromatography. A similar procedure can be used to obtain 2-substituted benzothiazole derivatives from o-aminothiophenol and the same set of carboxylic acids.

In various aspects, 2-substituted benzimidazoles can be prepared using the procedure of Ryabukhin et al. (e.g., a procedure as described in *J Org Chem,* 2007, 72 (19): 7417-7419) can be used. Briefly, different aldehydes can be individually aliquoted into multi-well plates. Each well can be supplemented with 1,2-diaminobenzene and DMF. TMSCl can be added dropwise to the solution, and each well can be sealed and the mixtures heated for 4 hours. After cooling, each reaction mixture can be precipitated with water and recrystallized from an appropriate solvent.

Compounds according to the present disclosure can, for example, be prepared by the several methods outlined below. A practitioner skilled in the art will understand the appropriate use of protecting groups [see: Greene and Wuts, *Protective Groups in Organic Synthesis*] and the preparation of known compounds found in the literature using the standard methods of organic synthesis. There may come from time to time the need to rearrange the order of the recommended synthetic steps, however this will be apparent to the judgment of a chemist skilled in the art of organic synthesis. The following examples are provided so that the invention might be more fully understood, are illustrative only, and should not be construed as limiting.

In one aspect, the disclosed compounds comprise the products of the synthetic methods described herein. In a further aspect, the disclosed compounds comprise a compound produced by a synthetic method described herein. In a still further aspect, the invention comprises a feed composition comprising an effective amount of the product of the disclosed methods and a feed component. In an even further aspect, the feed component is selected from a vegetable protein, a fat-soluble vitamin, a water-soluble vitamin, a trace mineral, and a macro mineral. In a still further aspect, the feed component is water.

1. Route I

In one aspect, substituted benzothiazole and benzoxazole analogs can be prepared as shown below.

SCHEME 1A.

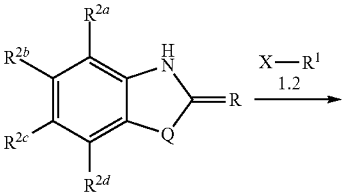

1.1

-continued

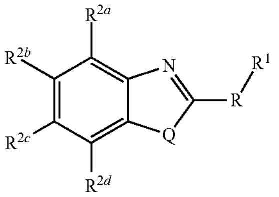

1.3

Compounds are represented in generic form, with substituents as noted in compound descriptions elsewhere herein, wherein R is selected from S and O, and wherein X is halogen. A more specific example is set forth below.

SCHEME 1B.

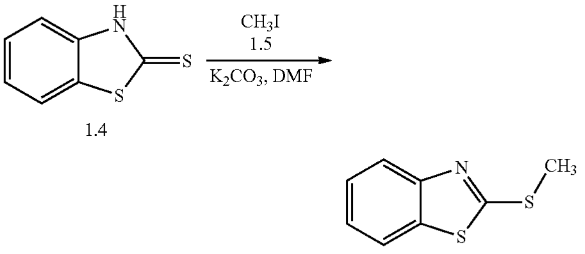

1.4

1.6

In one aspect, compounds of type 1.6, and similar compounds, can be prepared according to reaction Scheme 1B above. Thus, compounds of type 1.5 can be prepared by an alkylation of an appropriate thione, e.g., 1.4 as shown above. Appropriate thiones are commercially available or prepared by methods known to one skilled in the art. The alkylation is carried out in the presence of an appropriate alkyl halide, e.g., 1.5 as shown above, and an appropriate base, e.g., potassium carbonate, in an appropriate solvent, e.g., dimethylformamide. As can be appreciated by one skilled in the art, the above reaction provides an example of a generalized approach wherein compounds similar in structure to the specific reactants above (compounds similar to compounds of type 1.1 and 1.2), can be substituted in the reaction to provide substituted benzothiazole and benzoxazole analogs similar to Formula 1.3.

2. Route II

In one aspect, aryl substituted benzothiazole and benzoxazole analogs can be prepared as shown below.

SCHEME 2A.

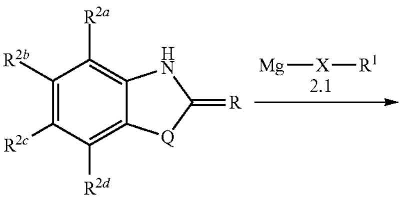

1.1

-continued

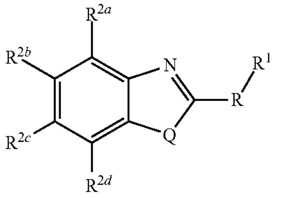

1.3

Compounds are represented in generic form, with substituents as noted in compound descriptions elsewhere herein, wherein R is selected from S and O, and wherein X is halogen. A more specific example is set forth below.

SCHEME 2B.

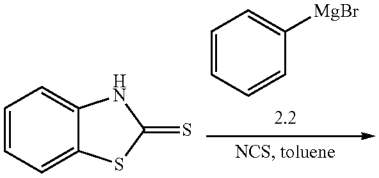

1.4

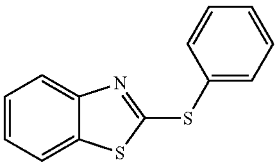

2.3

In one aspect, compounds of type 2.3, and similar compounds, can be prepared according to reaction Scheme 2B above. Thus, compounds of type 1.6 can be prepared by an arylation of an appropriate thione, e.g., 1.4 as shown above. Appropriate thiones are commercially available or prepared by methods known to one skilled in the art. The arylation is carried out in the presence of an appropriate Grignard reagent, e.g., 2.2 as shown above, and an appropriate oxidizing agent, e.g., N-chlorosuccinimide (NCS), in an appropriate solvent, e.g., toluene. As can be appreciated by one skilled in the art, the above reaction provides an example of a generalized approach wherein compounds similar in structure to the specific reactants above (compounds similar to compounds of type 1.1 and 2.1), can be substituted in the reaction to provide aryl substituted benzothiazole and benzoxazole analogs similar to Formula 2.3.

3. Route III

In one aspect, N-substituted benzothiazol-2-amine analogs can be prepared as shown below.

SCHEME 3A.

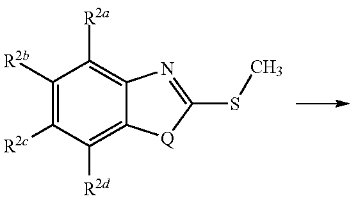

3.1

-continued

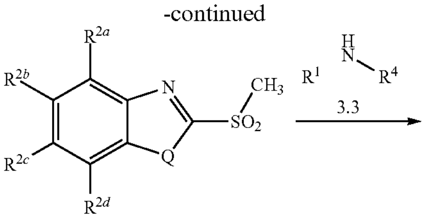

3.2

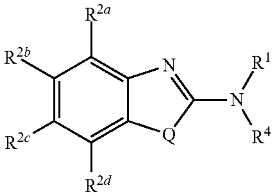

3.4

Compounds are represented in generic form, with substituents as noted in compound descriptions elsewhere herein. A more specific example is set forth below.

SCHEME 3B.

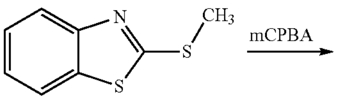

1.6

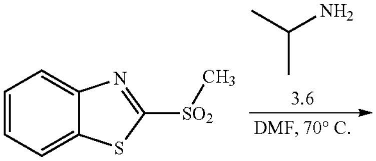

3.5

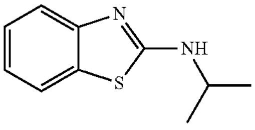

3.7

In one aspect, compounds of type 3.7, and similar compounds, can be prepared according to reaction Scheme 3B above. Thus, compounds of type 3.5 can be prepared by oxidation of an appropriate thioalkyl, e.g., 1.6 as shown above. Appropriate thioalkyls are commercially available or prepared by methods known to one skilled in the art. The oxidation is carried out in the presence of an appropriate oxidant, e.g., m-chloroperoxybenzoic acid (m-CPBA). Compounds of type 3.7 can be prepared by a displacement reaction of an appropriate sulfonylalkyl, e.g., 3.5 as shown above. The displacement reaction is carried out in the presence of an appropriate amine, e.g., 3.6 as shown above, in an appropriate solvent, e.g., dimethylformamide, at an appropriate temperature, e.g., 70° C. As can be appreciated by one skilled in the art, the above reaction provides an example of a generalized approach wherein compounds similar in structure to the specific reactants above (compounds similar to compounds of type 3.1, 3.2, and 3.3), can be substituted in the reaction to provide N-substituted benzothiazol-2-amines similar to Formula 3.4.

F. Methods for Preventing a Disease Caused by Infection by *C. perfringens* in a Subject In one aspect, disclosed are methods for preventing a disease caused by infection by *Clostridium perfringens* in a subject, the method comprising administering to the subject an effective amount of a compound having a structure represented by a formula:

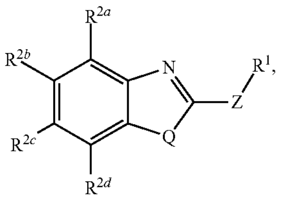

wherein Q is selected from O, S, and $NR^3$; wherein $R^3$, when present, is selected from hydrogen and C1-C8 alkyl; wherein Z is selected from O, S, and $NR^4$; wherein $R^4$, when present, is selected from hydrogen and C1-C8 alkyl; wherein $R^1$ is selected from hydrogen, C1-C8 alkyl, C1-C8 haloalkyl, $—CR^{5a}R^{5b}(C{=}O)NHN{=}CR^6Ar^1$, $Cy^1$, and $Ar^2$, provided that if Q is $NR^3$ then $R^1$ is not $—CR^{5a}R^{5b}(C{=}O)R^5$; wherein each of $R^{5a}$ and $R^{5b}$, when present, is independently selected from hydrogen and C1-C4 alkyl; wherein $R^6$, when present, is selected from hydrogen and C1-C4 alkyl; wherein $Cy^1$ is selected from C3-C7 cycloalkyl and C2-C7 heterocycloalkyl and substituted with 0, 1, or 2 groups independently selected from halogen, —OH, —CN, $—NO_2$, $—NH_2$, C1-C4 alkyl, C1-C4 alkoxy, C1-C4 haloalkyl, C1-C4 alkylamino, and (C1-C4)(C1-C4) dialkylamino; wherein $Ar^1$ is selected from aryl and heteroaryl and substituted with 0, 1, or 2 groups independently selected from halogen, —OH, —CN, $—NO_2$, $—NH_2$, C1-C4 alkyl, C1-C4 alkoxy, C1-C4 haloalkyl, C1-C4 alkylamino, and (C1-C4)(C1-C4) dialkylamino; wherein $Ar^2$ is selected from aryl and heteroaryl and substituted with 0, 1, or 2 groups independently selected from halogen, —OH, —CN, $—NO_2$, $—NH_2$, C1-C4 alkyl, C1-C4 alkoxy, C1-C4 haloalkyl, C1-C4 alkylamino, and (C1-C4)(C1-C4) dialkylamino; and wherein each of $R^{2a}$, $R^{2b}$, $R^{2c}$, and $R^{2d}$ is independently selected from hydrogen, halogen, —OH, —CN, $—NO_2$, $—NH_2$, C1-C4 alkyl, C1-C4 alkoxy, C1-C4 haloalkyl, C1-C4 alkylamino, and (C1-C4)(C1-C4) dialkylamino, thereby preventing the disease caused by infection by *Clostridium perfringens* in a subject.

G. Methods for Inhibiting Germination of at Least One *C. perfringens* Spore

This document also provides methods for inhibiting germination of *C. perfringens* spores in the gut of animals (e.g., domesticated or farmed fowl such as, without limitation, chickens, turkeys, ducks, and geese). The administration of such compounds and compositions thus can prevent or reduce the likelihood of occurrence of NE in an animal containing intestinal *C. perfringens* spores, reduce the occurrence of NE in a population of animals in which at least some of the animals contain intestinal *C. perfringens* spores, and treat the occurrence of NE in an animal in which *C. perfringens* spores have germinated (e.g., to reduce or prevent transmission of the disease to other animals).

Thus, also disclosed are methods for inhibiting germination of at least one *Clostridium perfringens* spore, the method comprising contacting the spore with a compound having a structure represented by a formula:

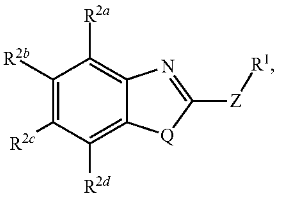

wherein Q is selected from O, S, and $NR^3$; wherein $R^3$, when present, is selected from hydrogen and C1-C8 alkyl; wherein Z is selected from O, S, and $NR^4$; wherein $R^4$, when present, is selected from hydrogen and C1-C8 alkyl; wherein $R^1$ is selected from hydrogen, C1-C8 alkyl, C1-C8 haloalkyl, $—CR^{5a}R^{5b}(C{=}O)NHN{=}CR^6Ar^1$, $Cy^1$, and $Ar^2$, provided that if Q is $NR^3$ then $R^1$ is not $—CR^{5a}R^{5b}(C{=}O)R^5$; wherein each of $R^{5a}$ and $R^{5b}$, when present, is independently selected from hydrogen and C1-C4 alkyl; wherein $R^6$, when present, is selected from hydrogen and C1-C4 alkyl; wherein $Cy^1$ is selected from C3-C7 cycloalkyl and C2-C7 heterocycloalkyl and substituted with 0, 1, or 2 groups independently selected from halogen, —OH, —CN, $—NO_2$, $—NH_2$, C1-C4 alkyl, C1-C4 alkoxy, C1-C4 haloalkyl, C1-C4 alkylamino, and (C1-C4)(C1-C4) dialkylamino; wherein $Ar^1$ is selected from aryl and heteroaryl and substituted with 0, 1, or 2 groups independently selected from halogen, —OH, —CN, $—NO_2$, $—NH_2$, C1-C4 alkyl, C1-C4 alkoxy, C1-C4 haloalkyl, C1-C4 alkylamino, and (C1-C4)(C1-C4) dialkylamino; wherein $Ar^2$ is selected from aryl and heteroaryl and substituted with 0, 1, or 2 groups independently selected from halogen, —OH, —CN, $—NO_2$, $—NH_2$, C1-C4 alkyl, C1-C4 alkoxy, C1-C4 haloalkyl, C1-C4 alkylamino, and (C1-C4)(C1-C4) dialkylamino; and wherein each of $R^{2a}$, $R^{2b}$, $R^{2c}$, and $R^{2d}$ is independently selected from hydrogen, halogen, —OH, —CN, $—NO_2$, $—NH_2$, C1-C4 alkyl, C1-C4 alkoxy, C1-C4 haloalkyl, C1-C4 alkylamino, and (C1-C4)(C1-C4) dialkylamino, thereby inhibiting germination of at least one *Clostridium perfringens* spore.

The methods can include administering to one or more animal a compound or composition in an amount effective to reduce or prevent germination of *C. perfringens*, as described herein. In various aspects, an effective amount can be from about 0.1 nmol to about 100 mmol (e.g., about 0.1 nmol to about 1 nmol, about 1 nmol to about 10 nmol, about 10 nmol to about 0.1 mmol, about 0.1 mmol to about 1 mmol, about 1 mmol to about 5 mmol, about 5 mmol to about 10 mmol, about 10 mmol to about 50 mmol, or about 50 mM to about 100 mmol). In the methods provided herein, the compound(s), composition(s), and/or feed can be administered any number of times during the life of the animal, although it is noted that administration throughout the life of the animal can be useful. Thus, using feed containing one or more compounds as described herein may be particularly useful, as the recipient animal would essentially self-administer the compound(s) simply by eating.

The invention will be further described in the following examples, which do not limit the scope of the invention described in the claims.

H. Examples

*C. perfringens* spore germination can produce different and sometimes contradictory results. See, e.g., (Kato et al.,

*J Biosci Bioeng* 2009, 108 (6): 477-483; Paredes-Sabja et al., *J Bacteriol* 2008, 190 (4): 1190-1201; and Paredes-Sabja et al., *Appl Envir Microbiol* 2009, 75 (19): 6299-6305). As described in the Examples below, the requirements for spore germination was analyzed in seven *C. perfringens* strains. These studies showed that *C. perfringens* spores can germinate using two distinct pathways. The first germination pathway (AA) requires L-alanine/L-phenylalanine as co-germinants. The AA pathway is enhanced by L-arginine and blocked by L-tryptophan. The second germination pathway (BA) is more promiscuous, and is activated by a number of bile salts and amino acids (FIG. 1).

As further described herein, analogs of L-tryptophan and indole were tested as inhibitors of *C. perfringens* spores germinated using either the AA or BA pathway. Tryptophan analogs inhibited *C. perfringens* spores from germinating through the AA pathway, while indole analogs inhibited *C. perfringens* spores from germinating through the BA pathway. Six other heteroaromatic compounds were found to strongly inhibit both germination pathways. The strongest inhibitors, 2-methoxy benzothiazole (MOB, $IC_{50}$=98 pM) and 2-methylthiobenzothiazole (2-MTB, $IC_{50}$=74 pM), were found to inhibit at concentrations approximately ten times lower than other analogs.

1. General Experimental Methods

All chemicals were purchased from Sigma-Aldrich Corp. (St. Louis, MO). Thioglycollate medium, peptones, yeast extract, raffinose and agar were purchased from VWR (Radnor, PA). *C. perfringens* strains JGS1936, JGS1473, JGS1882, JGS1521, JGS4104, JGS4151, and JGS 4064 (Barbara et al., Vet Microbiol 2008, 126:377-382) were obtained from Professor J. Glenn Songer (Iowa State University, Ames, IA). The identities of selected *C. perfringens* spore preparations were confirmed by 16S RNA sequencing.

2. Testing of Growth Conditions on *C. perfringens* Sporulation Yields

*C. perfringens* strains were plated on 2% agar supplemented with 1% yeast extract, 0.1% sodium thioglycollate, 1.5% protease peptone, and 60 mM $Na_2HPO_4$. Plates were incubated overnight in an anaerobic environment (5% $CO_2$, 5% $H_2$, 90% $N_2$). Single-cell clones were picked and grown for four hours in either thioglycollate medium or BHI broth. All *C. perfringens* strains were then plated on 2% agar supplemented with 1% yeast extract, 0.1% sodium thioglycollate, 60 mM $Na_2HPO_4$, and 1.5% of a peptone source (protease peptone #1, protease peptone #2, protease peptone #3, or potato peptone). Media also were supplemented with 0.5% of a filter-sterilized carbon source (glucose, starch, or raffinose). Some plates were supplemented with theobromine to 0.01% final concentration. Plates were incubated for up to 14 days at 37° C. under anaerobic conditions. Sporulation was quantified by microscopy observation of culture samples stained using the Schaeffer-Fulton method (Hamouda et al., *Lett Appl Microbiol* 2002, 34:86-90). Under these conditions, spores are stained green and vegetative cells are stained red. The approximate number of green spores and red vegetative cells were counted in at least three independent microscopy fields selected at random. A high level of sporulation was defined as >40% spores. A medium level of sporulation was defined as 20-40% spores. A low level of sporulation was defined as <20% spores.

3. Purification of *C. perfringens* Spores

Each *C. perfringens* strain was plated under their best sporulation conditions (Table 1). Plates were incubated for 5-10 days at 37° C. in an anaerobic environment. The resulting bacterial lawns were collected by flooding with ice-cold deionized water. Spores were pelleted by centrifugation and resuspended in fresh deionized water. After two washing steps, spores were separated from vegetative and partially sporulated cells by centrifugation through a 20%-50% HistoDenz gradient. Spore pellets were washed five times with water, resuspended in 0.1% sodium thioglycollate and stored at 4° C. All spore preparations were more than 95% pure as determined by microscopy observation of Schaeffer-Fulton stained aliquots.

4. Preparation of Germinant Solution

AGFK mixture (10 mM L-asparagine, 10 mM D-glucose, 10 mM D-fructose, 50 mM KCl) was prepared as previously described (Wax and Freese, *J Bacteriol* 1968, 95:433-438). The defined medium employed was described elsewhere (Ramirez and Abel-Santos, *J Bacteriol* 2010, 192:418-425). Briefly, a buffer solution was made with 6.6 mM $KH_2PO_4$, 15 mM NaCl, 59.5 mM $NaHCO_3$, and 35.2 mM $Na_2HPO_4$. Three solutions were prepared in using this buffer as diluent. The first solution contained all salts at 1000× concentrations (final concentration were 10 mg/l $MgSO_4·7H_2O$, 5 mg/l $FeSO_4·7H_2O$, 5 mg/l $MnCl_2·4H_2O$). The second solution contained vitamins at 10× concentrations (final 132 concentrations were 0.05 mg/l D-biotin, 0.1 mg/l p-amino benzoic acid, 0.05 mg/l thiamine hydrochloride, 0.05 mg/l pyridoxine, and 1.0 mg/l nicotinic acid). The third solution contained all amino acids except cysteine at 10× (final concentrations were 10 mM for each amino acid). Cysteine was prepared separately as a 10× solution in 0.2 N HCl. To prepare the defined medium, different solutions were added to buffer at the final concentrations indicated. In some samples, inosine was added to 1 mM final concentration.

To determine individual germinants, stock (10×) solutions of L-amino acids, $NaHCO_3$, $KHCO_3$, KCl, KBr, NaCl, NaBr, and bile salts were individually prepared in deionized sterile water. Combinations of these solutions were tested to determine germinants necessary for *C. perfringens* spore germination. Table 1 below illustrates the source and optimal sporulation conditions for each *C. perfringens* strain.

TABLE 1

| Strain | Source | Inoculum | Peptone | Theobromine |
|---|---|---|---|---|
| 1936 | Bovine neonatal enteritis | BHI | #1 | No effect on sporulation |
| 1882 | Porcine necrotic enteritis | BHI | #2 | Increases sporulation |
| 1473 | Chicken normal flora | Thioglycollate | #1 | Reduces sporulation |
| 1473 | Chicken normal flora | BHI | #3 | Increases sporulation |
| 1521 | Chicken necrotic enteritis | Thioglycollate | #1 | Required for sporulation |
| 4064 | Chicken necrotic enteritis | BHI | #1 | Required for sporulation |
| 4104 | Turkey necrotic enteritis | BHI | #3 | Required for sporulation |
| 4104 | Turkey necrotic enteritis | Thioglycollate | #3 | Required for sporulation |
| 4121 | Human gas gangrene | Thioglycollate | #2 | Required for sporulation |

I. Requirements for *C. perfringens* Spore Sermination

Changes in light diffraction during spore germination were monitored at 580 nm ($OD_{580}$) on a Tecan Infinite M200 96-well 144 plate reader (Tecan group, Mannedorf, Switzerland). *C. perfringens* spores were heat-activated at 65° C. for 30 minutes (Desrosier, and Heiligman, *Food Res* 1956, 21:54-62). The spore suspension was cooled to room temperature and monitored for auto-germination for 30 minutes. Germination experiments were carried out with spores that did not auto-germinate. After heat activation, spores were resuspended to an $OD_{580}$ of 1 in AGFK, LB broth, or defined medium. Spore germination rates were evaluated based on the decrease in $OD_{580}$ at room temperature. After germinant additions, $OD_{580}$ was measured at 1 minute intervals for 90 minutes. Relative $OD_{580}$ values were derived by dividing each $OD_{580}$ reading by the initial $OD_{580}$. Experiments were performed in triplicate with at least two different spore preparations. Germination rates were calculated from the initial linear region of the germination curves. Standard deviations were calculated from at least six independent measurements and were typically below 20%. Germination was confirmed in selected samples by microscopy observation of Schaeffer-Fulton stained aliquots.

To determine amino acid co-germinants, *C. perfringens* spores were resuspended in germination buffer (0.1 mM sodium phosphate buffer (pH 6.5), 50 mM $NaHCO_3$) to an $OD_{580}$ of 1. Putative germinants were added individually or in combinations to a final concentration of 10 mM. After addition of germinants, spore germination was monitored by the decrease in optical density at 580 nm, as above. Germination rates were set to 100% for *C. perfringens* spores germinated in the presence of L-alanine and L-phenylalanine. Relative germination for other germinant combinations was calculated as the fraction of germination rate compared to germination with L-alanine/L-phenylalanine.

To determine bile salt co-germinants, *C. perfringens* spores were resuspended in potassium phosphate buffer (pH 6.5) supplemented with 5% $KHCO_3$, and 150 mM KCl. Spore germination was started by addition of 6 mM taurocholate, and 6 mM individual amino acids. *C. perfringens* spores were also germinated with 6 mM L-alanine and 6 mM individual bile salts. After addition of germinants, spore germination was monitored as above. Germination rates were set to 100% for *C. perfringens* spores germinated in the presence of L-alanine and taurocholate. Relative germination for other germinant combinations was calculated as the fraction of germination rate compared to germination with L-alanine/taurocholate.

5. Testing for Inhibitors of C. *Perfringens* Spore Germination

*C. perfringens* spores were resuspended in sodium phosphate buffer (pH 6.5) supplemented with 5% $NaHCO_3$, and 150 mM NaCl (for the AA pathway) or potassium phosphate buffer (pH 6.5) supplemented with 5% $KHCO_3$, and 150 mM KCl (for the BA pathway). Spore samples were then individually supplemented with 6 mM amino acid or 6 mM bile salt analogs. Spore suspensions were incubated for 15 minutes at room temperature while the $OD_{580}$ was monitored. If no germination was detected, spores were supplemented with 6 mM L-alanine/6 mM L-phenylalanine (for the AA pathway) or 6 mM L-alanine/6 mM taurocholate (for the BA pathway). Germination rates were set to 100% for *C. perfringens* spores germinated in the absence of inhibitor. Relative germination for conditions was calculated as the fraction of germination rate compared to no inhibitor.

6. Effect of Buffer and pH on C. *Perfringens* Spore Germination

Individual *C. perfringens* spore aliquots were individually resuspended in 0.1 M sodium phosphate buffer (or 0.1 M potassium phosphate buffer) and pH levels were individually adjusted between 5.5 and 8.0. Germination was started by addition of 6 mM L-alanine/6 mM L-phenylalanine (for the AA pathway) or 6 mM L-alanine/6 mM taurocholate (for the BA pathway). Spore germination was monitored as above. For the AA pathway, the germination rate was set to 100% for *C. perfringens* spores germinated at pH 6.5 in sodium phosphate buffer. For the BA pathway, the germination rate was set to 100% for *C. perfringens* spores germinated at pH 6.5 in potassium phosphate buffer. The percentage of germination for other conditions was calculated as a fraction of the rate of germination at pH 6.5.

7. Effect of Cations and Anions on *C. perfringens* Spore Germination

*C. perfringens* spores were individually incubated for five minutes in 0.1 M sodium phosphate buffer, pH 6.5 or 0.1 M potassium phosphate buffer, pH 6.5. Samples were then individually supplemented with 150 mM KCl, KBr, NaCl, NaBr, $KHCO_3$, or $NaHCO_3$. Germination was started by addition of 6 mM L-alanine/6 mM L-phenylalanine (for the AA pathway) or 6 mM L-alanine/6 mM taurocholate (for the BA pathway). Spore germination was monitored by the decrease in optical density, as above. For the AA pathway, the germination rate was set to 100% for *C. perfringens* spores germinated in sodium phosphate buffer without added salts. For the BA pathway, the germination rate was set to 100% for *C. perfringens* spores germinated in potassium phosphate buffer without added salts. The percentage of germination for other conditions was calculated as a fraction of the rate in the absence of added salts.

8. Effect of Sporulation Media on *C. perfringens* Spore Germination

Sporulation conditions can affect the germination response of bacterial spores (Hornstra et al., *Appl Environ Microbiol* 2006, 72:3746-3749; and Ramirez-Peralta et al., *Appl Environ Microbiol* 2011, 78:2689-2697). To test if *C. perfringens* spore germination could be modulated by sporulation media, a matrix of conditions for sporulation was created with combinations of different liquid media, solid media, carbon sources, peptones, and additives for every *C. perfringens* strain used in the study (Table 2).

All *C. perfringens* strains tested sporulated in solid media, but not in liquid media. However, it was observed that sporulation was dependent upon which liquid media was used for overnight growth prior to plating in agar (Table 2). For strains JG 1936, JG 1882, JG4064, overnight growth in BHI was necessary to induce sporulation upon replating in the correct solid media. Other strains (JGS 1521, JG4121), required overnight growth in liquid thioglycollate medium to induce sporulation in agar. For other strains (JGS 1473, JG41 04), the liquid media used for overnight growth changed the preference of solid media required for sporulation.

TABLE 2

| | Replated from BH1 Peptone number | | | | | | Replated from Thioglycollate Peptone number | | | | | |
|---|---|---|---|---|---|---|---|---|---|---|---|---|
| Strain | #1 | #2 | #3 | #1* | #2* | #3* | #1 | #2 | #3 | #1* | #2* | #3* |
| 1936 | +++ | – | – | +++ | – | – | – | – | – | – | – | – |
| 1882 | – | ++ | – | – | +++ | – | – | – | – | – | – | – |
| 4064 | – | – | – | +++ | – | – | – | – | – | – | – | – |
| 1521 | – | – | – | – | – | – | – | – | – | +++ | – | – |
| 4121 | – | – | – | – | – | – | – | – | – | – | +++ | – |
| 1473 | – | – | +++ | – | – | + | ++ | – | – | +++ | – | – |
| 4104 | – | – | – | – | – | +++ | – | – | – | – | + | +++ |

All *C. perfringens* strains were plated on 2% agar supplemented with 1% yeast extract, 0.1% sodium thioglycollate, 60 mM Na2HPO4, 0.5% raffinose, and 1.5% of a peptone source.
*Plates also were supplemented with theobromine to 0.01% final concentration;
+++, >40% spores;
++, 20-40% spores;
+, <20% spores;
–, no detectable spores.

Glucose, starch, and raffinose were tested as carbon sources for sporulation. Consistent with results described elsewhere, raffinose was the preferred carbon source for *C. perfringens* sporulation (de Jong et al., *J Food Protect* 2002, 65:1457-1462). In the present studies, glucose and starch induced poor sporulation under all conditions tested (Sacks, *Appl Environ Microbiol* 1983, 46:1169-1175).

Peptone sources have been shown to affect the level of sporulation in *C. perfringens* strains (Hsieh and Labbe *J Food Protect* 2007, 70:1730-1734). Peptone protease #1 induced sporulation in strains JGS 1936, JGS 1473, JGS4064, and JGS 1521. Peptone protease #2 was able to induce sporulation in strains JGS 1882 and JGS4121. Peptone protease #3 induced sporulation in JGS1473 and JGS41 04. Potato peptone can induce high levels of sporulation in some *C. perfringens* strains (Hsieh and Labbe, supra). In the present studies, however, potato peptone did not induce sporulation in any of the strains tested.

Theobromine can increase the levels of sporulation in *C. perfringens* strains, as described elsewhere (de Jong et al., supra). Indeed, strains JOS4104, JOS4064, JOS1521, and JOS4121 only sporulated robustly when theobromine was added to solid media. Strains JOS1936, JOS1882, and JOS1473 sporulated in the absence of theobromine. In the presence of theobromine, sporulation levels for strain JOS 1936 remained unchanged, increased for strain JOS 1882, and decreased for strain JOS1473.

Aside from differentially affecting sporulation levels, theobromine also reduced sporulation times in strains JOS1936, JOS1473, and JOS1882. In the absence of theobromine, sporulation was not detected until five days post-plating and maximum sporulation level was achieved 7-14 days post-plating. In the presence of theobromine, spores could be detected two days after plating and maximum sporulation levels were seen 5-7 days post-plating.

Contrary to work described elsewhere, *C. perfringens* spores failed to germinate with AOFK, KCL/L-asparagine, sodium/phosphate, or L-alanine/inosine mixtures (Kato et al., supra; Paredes-Sabja 2008, supra; and Paredes-Sabja 2009, supra). Like other *Clostridium* species, *C. perfringens* spores germinated efficiently in defined medium (FIG. 2A). *C. perfringens* spores germinated at the same rate in defined medium containing only amino acids. Henceforth, this germination response is referred to as the amino acid-only (AA) germination pathway.

9. Effect of Amino Acids on *C. perfringens* Spore Germination

To identify which amino acids are required for germination, *C. perfringens* spores were exposed to mixtures of small (L-Ala and Gly), polar (L-Ser, L-Thr, and L-Cys), hydrophobic (L-Leu, L-Ile, L-Met, and L-Val), aromatic (L-Phe, L-Tyr, and L-Trp), basic (L-Arg, L-Lys, and L-His), acidic (L-Asp and L-Glu), amide (L-Asn and L-Gln), or constrained (L-Pro) amino acids. None of these solutions alone was sufficient to trigger spore germination. *C. perfringens* spores were then resuspended in solutions containing pairs and trios of the above amino acid groups. *C. perfringens* spore germination was only observed in solutions containing mixtures of small and aromatic amino acids. Faster *C. perfringens* spore germination rates were observed when small and aromatic amino acids were supplemented with basic amino acids.

Figure 2A:
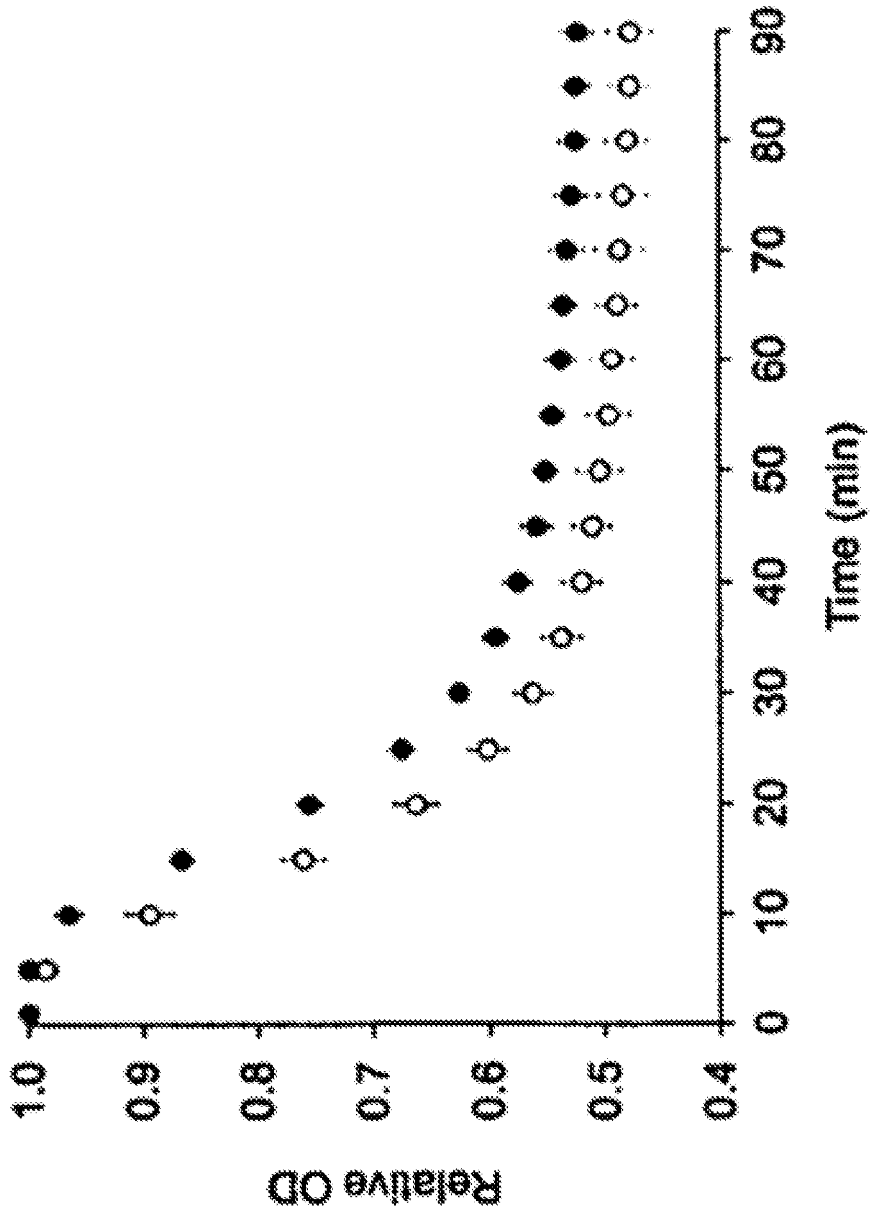
FIG. 2A and FIG. 2B show representative data illustrating that L-alanine/L-phenylalanine-mediated *C. perfringens* spore germination is potentiated by L-arginine and inhibited by L-tryptophan. Specifically.
Figure 2B:
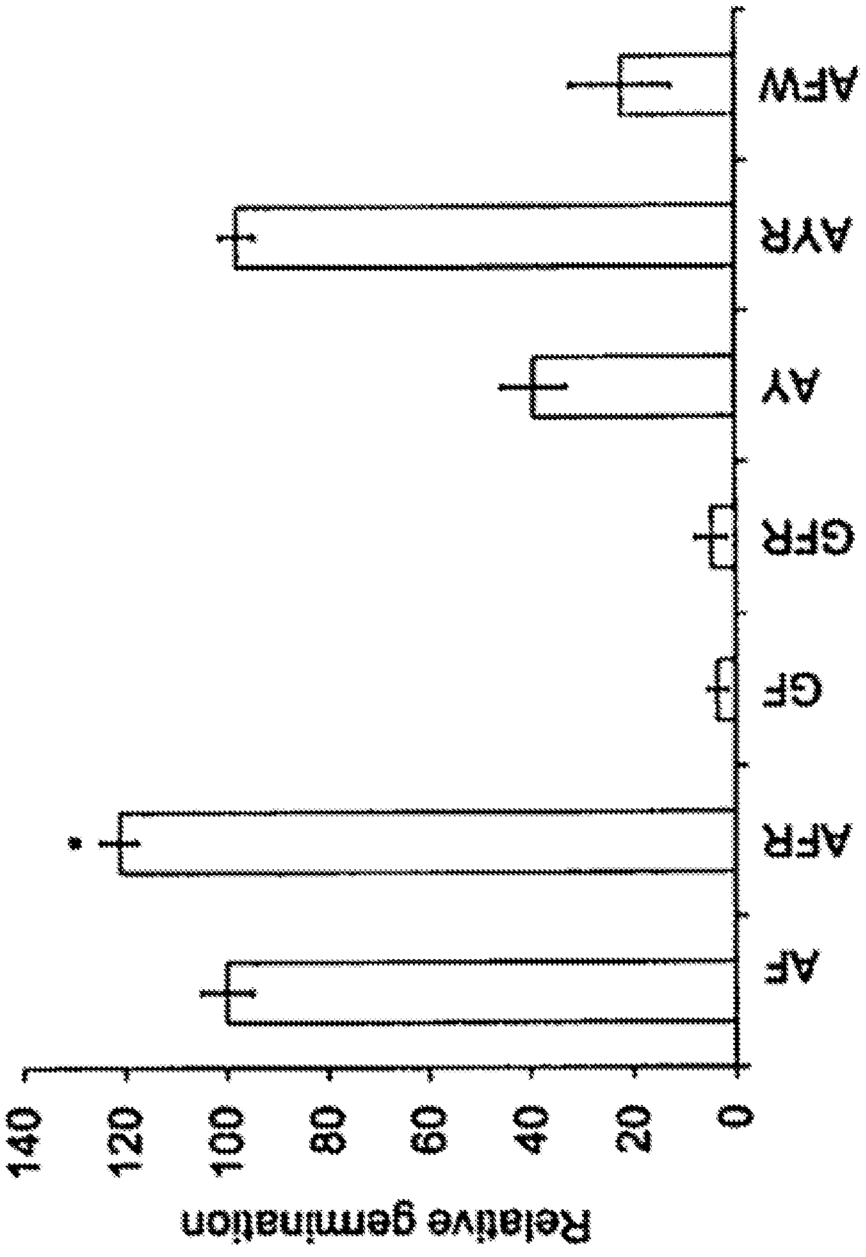

To further narrow the identity of L-amino acid germinants, all possible combinations of small, aromatic, and basic amino acids were tested individually for their effect on *C. perfringens* spore germination. For all strains tested, strong *C. perfringens* spore germination was seen in the presence of L-alanine/L-phenylalanine (FIG. 2A). L-arginine was not required to trigger germination, but increased germination rates by 20% (FIG. 2B). In the L-alanine/L-phenylalanine germination mixture, L-alanine could not be substituted for glycine, even in the presence of L-arginine. L-tyrosine could substitute L-phenylalanine, but the germination rate was more than 50% slower. Addition of L-arginine to L-alanine/L-tyrosine-treated spores increased germination rates more than 2-fold. *C. perfringens* spores did not respond to L-alanine/L-tryptophan mixtures. In fact, L-tryptophan behaved as an inhibitor of L-alanine/L-phenylalanine-mediated *C. perfringens* spore germination (FIG. 2B).

Figure 3A:
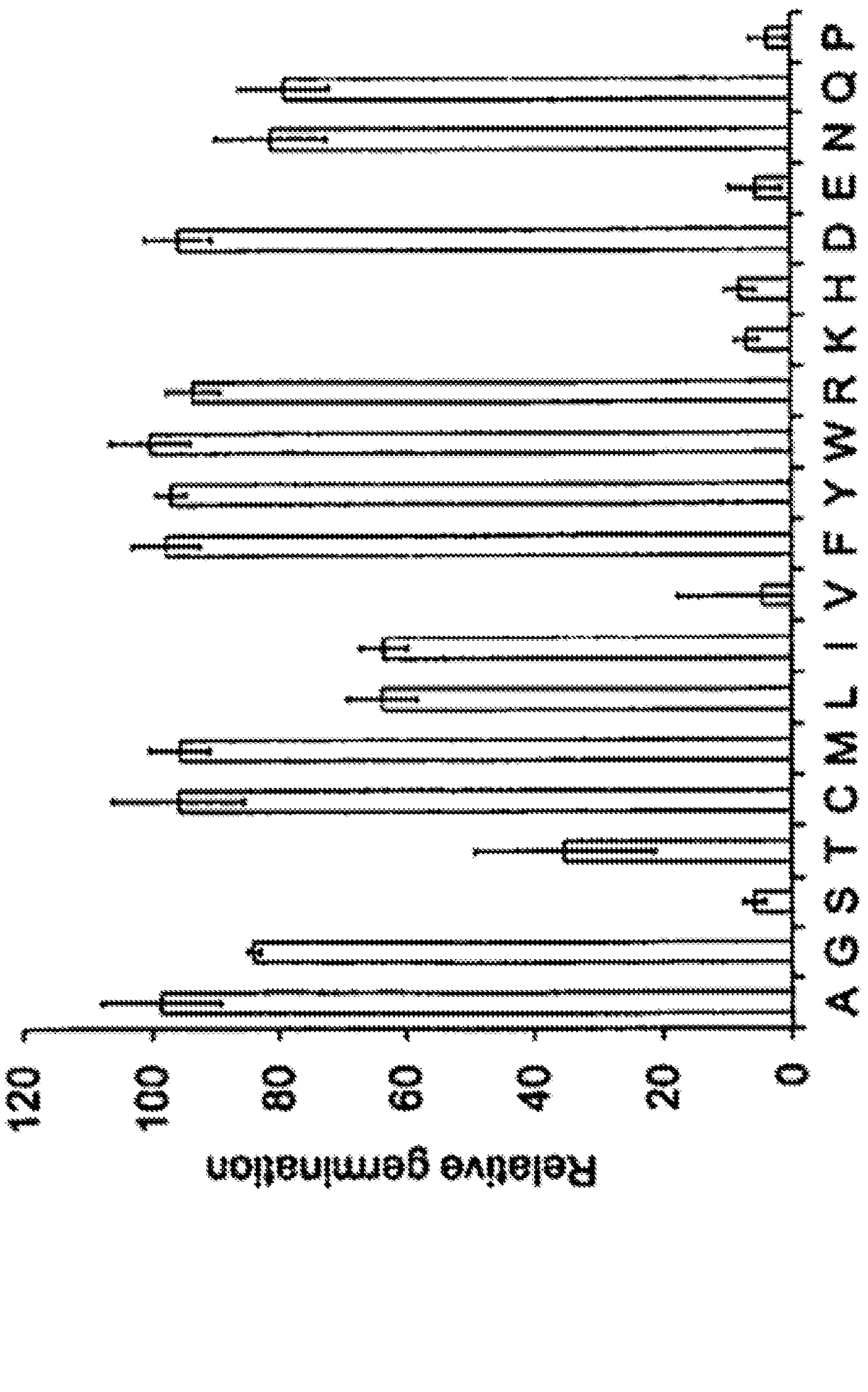
FIG. 3A and FIG. 3B show representative data illustrating that *C. perfringens* spores germinate with bile salts and amino acids. Specifically.
Figure 3B:
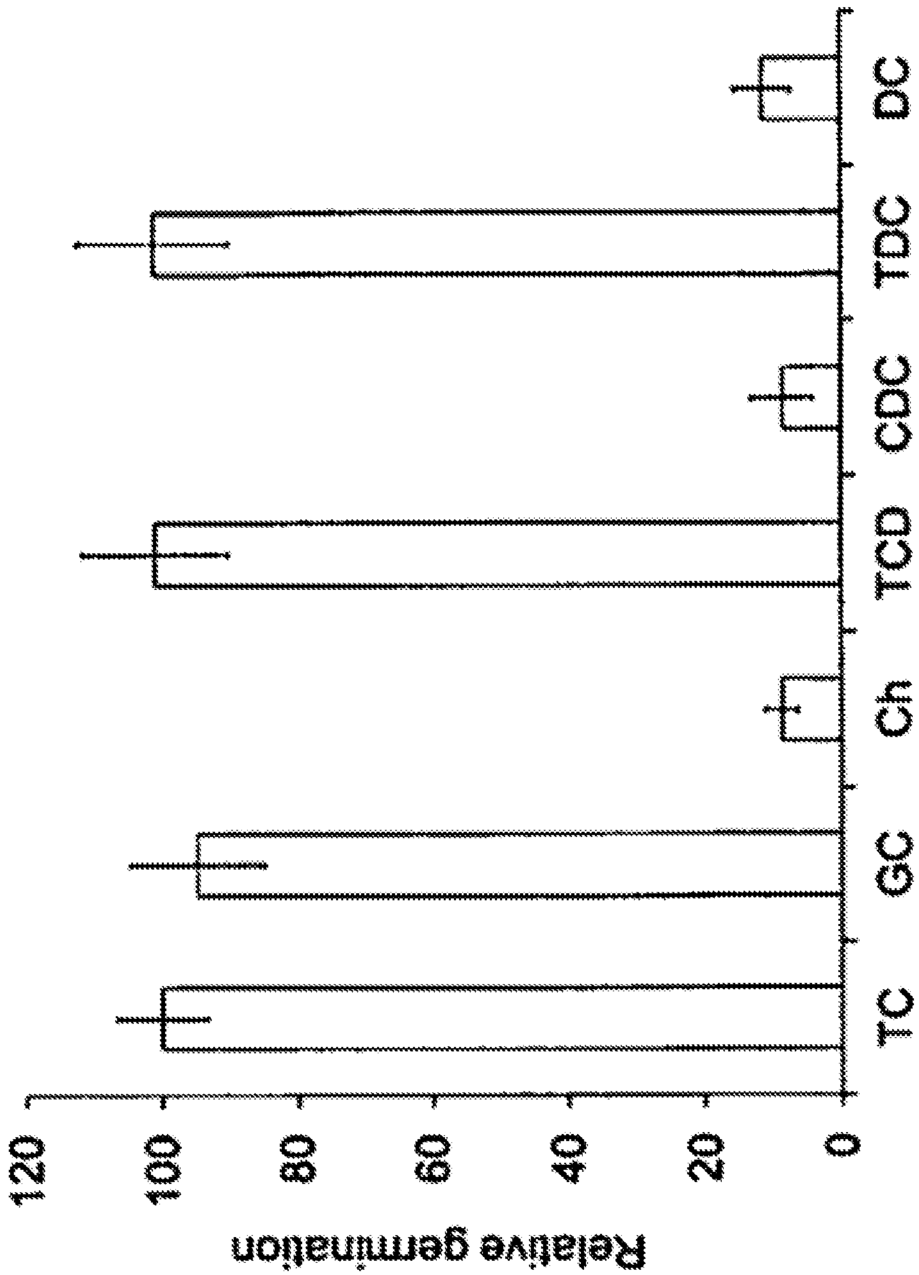

Sterane compounds can modulate the germination response of *C. difficile* and *C. sordellii* spores (Liggins et al, *J Bacteriol* 2011, 193:2776-2783). Taurocholate, a known co-germinant of *C. difficile* spores, was not sufficient to induce germination in *C. perfringens* spores. On the other hand, combinations of taurocholate and a variety of amino acids induced strong *C. perfringens* spore germination. In fact, only six amino acids did not synergize with taurocholate to induce significant *C. perfringens* spore germination (FIG. 3A). Glycocholate, taurochenodeoxycholate, and taurodeoxycholate also induced *C. perfringens* spore germination in the presence of amino acids. Cholate, chenodeoxycholate, and deoxycholate did not induce or inhibit *C. perfringens* spore germination in the presence of L-alanine (FIG. 3B). Henceforth, this germination response is referred to as the bile salt/amino acid (BA) germination pathway.

Because bile salts serve to solubilize dietary fats (Coleman, *Biochem Soc Trans* 1987, 15: 68S-80S), *C. perfringens* spores were treated with either SDS or Triton-X-100. Neither detergent was able to trigger *C. perfringens* spore germination, even in the presence of excess L-alanine.

D-amino acids can inhibit amino acid-mediated spore germination in *Bacillus* species (Yasuda and Tochikubo, *Microbiol Immunol* 1984, 28:197-207). D-alanine and D-arginine failed to inhibit or induce *C. perfringens* spore germination in the AA germination pathway, but D-phenylalanine and D-tryptophan both inhibited this pathway. In contrast, all the D-amino acids tested served as co-germinants with taurocholate in the BA pathway.

10. Optimal Conditions for *C. perfringens* Spore Germination

Figure 4A:
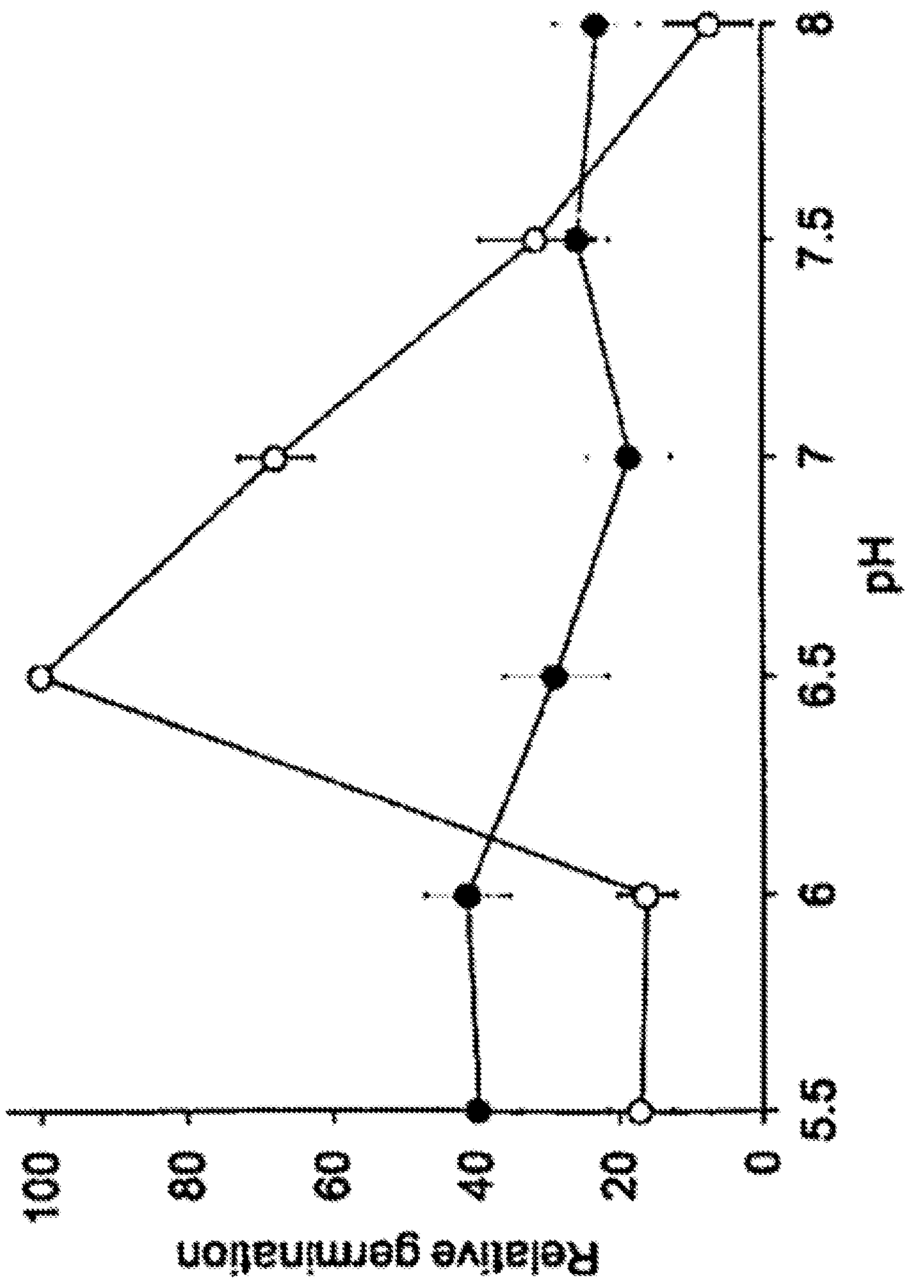
FIG. 4A-D show representative data illustrating the effect of pH and ions on *C. perfringens* spore germination. Specifically.
Figure 4B:
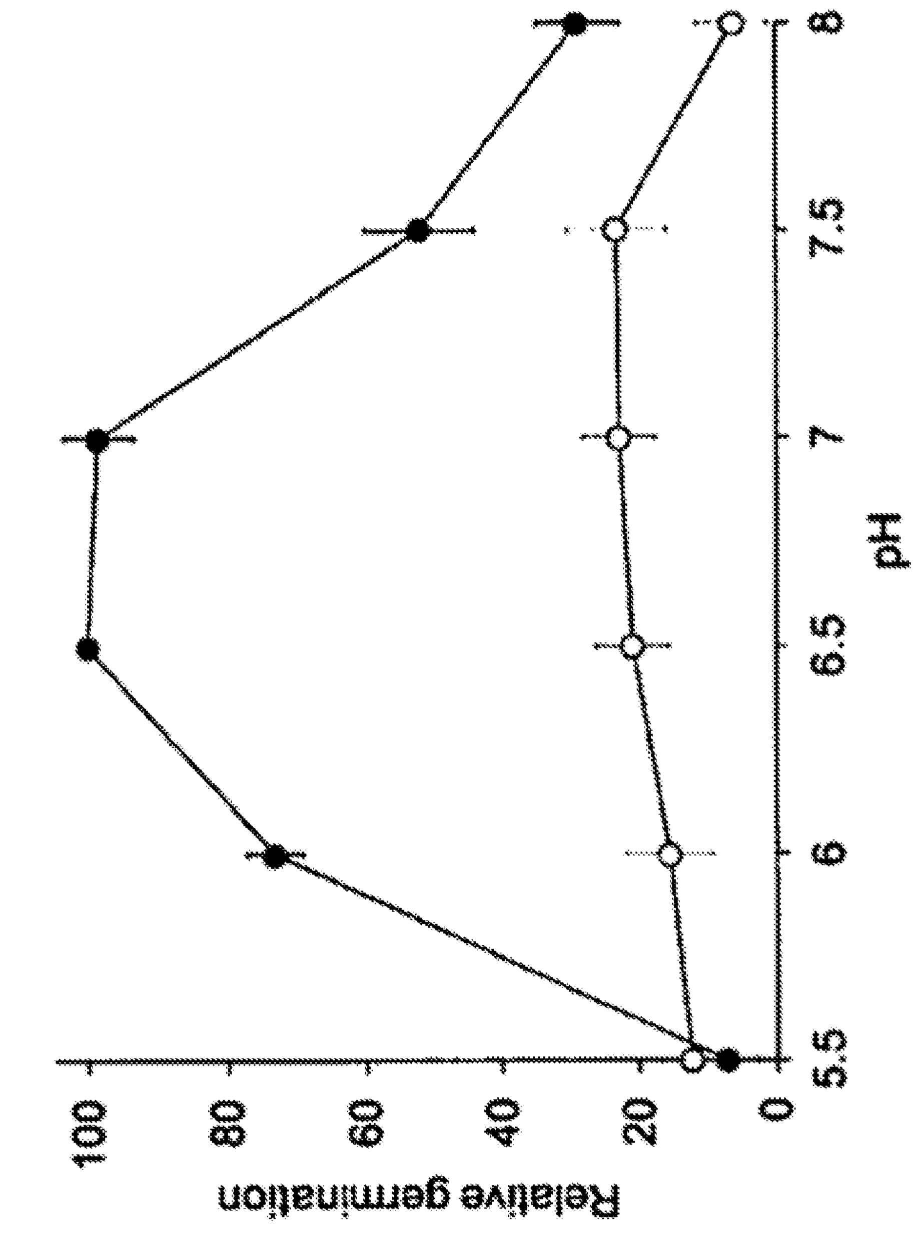

To define the optimal conditions for *C. perfringens* spore germination, spores were germinated at different pH levels. In the AA pathway, germination was significantly reduced if sodium phosphate buffer was substituted with potassium phosphate buffer (FIG. 4A). In contrast, the BA pathway was only active in the presence of potassium ions (FIG. 4B). For both pathways and in all strains, optimal germination occurred at near neutral to neutral pH. Germination was significantly reduced above pH 7.5 or below pH 5.5.

Figure 4C:
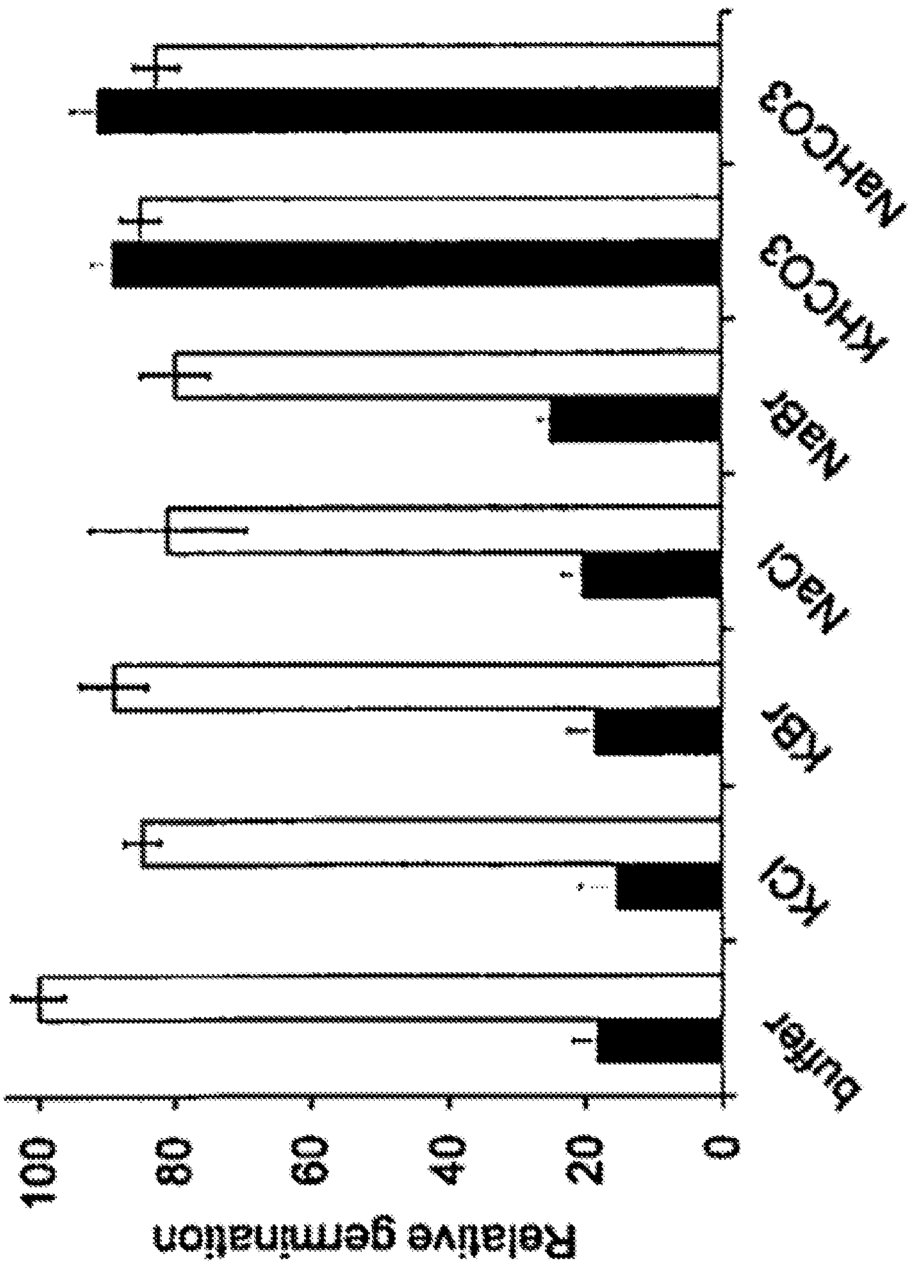
Figure 4D:
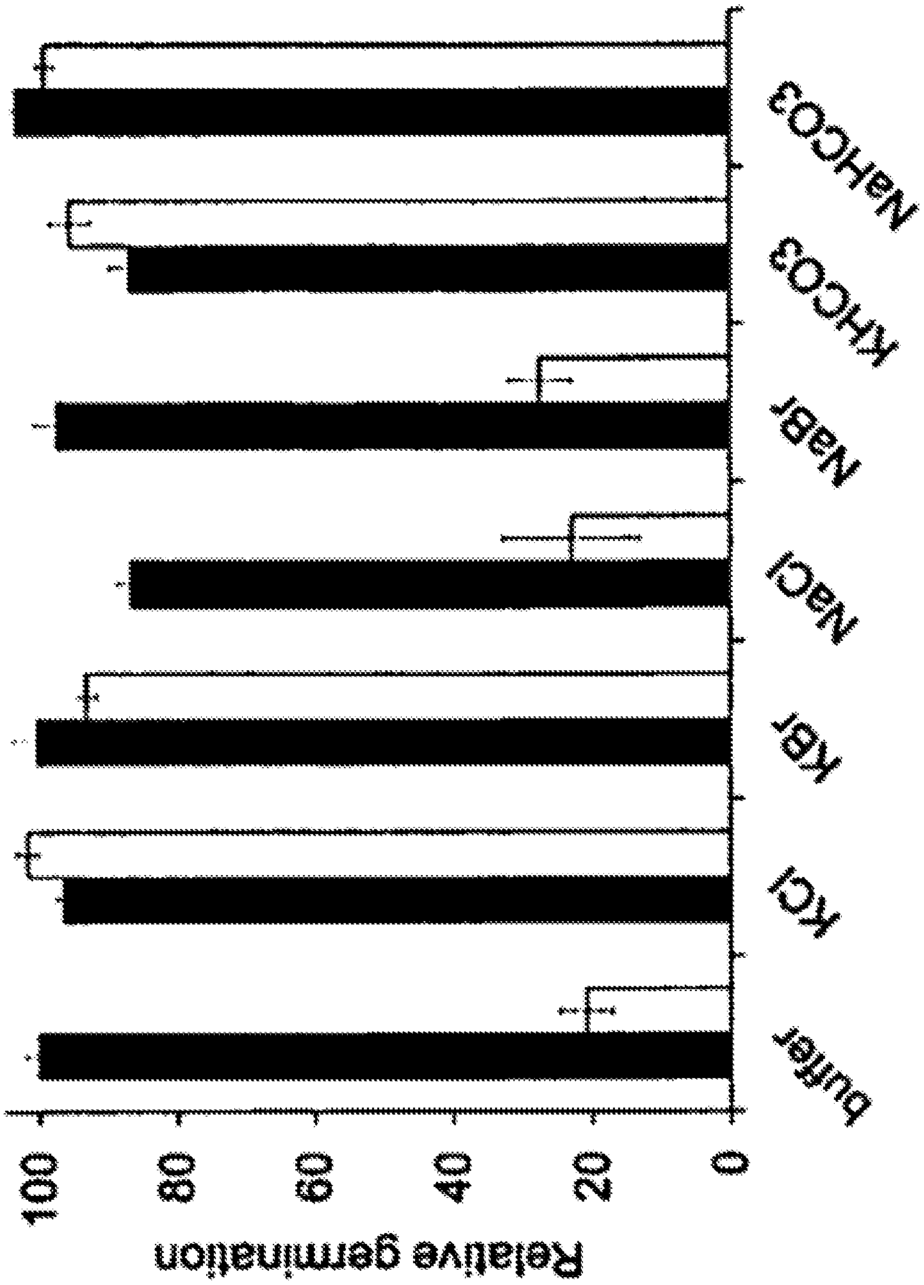

Interestingly, addition of KCl, KBr NaCl, or NaBr did not affect the AA pathway response in either potassium phosphate or sodium phosphate buffer (FIG. 4C). Similarly, NaCl and NaBr did not affect the BA germination pathway when spores were resuspended in potassium phosphate or sodium phosphate buffer. On the other hand, addition of KCl or KBr induced the BA pathway in spores resuspended in sodium phosphate buffer (FIG. 4D).

Bicarbonate is an essential co-germinant for some *Clostridium* species, as described elsewhere (Kato et al., supra; and, Ramirez and Abel-Santos 2010, supra). In both the AA and BA germination pathways, addition of potassium bicarbonate or sodium bicarbonate increased germination rate for *C. perfringens* spores resuspended in both potassium and sodium phosphate buffers (FIGS. 4C and 4D).

Because *C. perfringens* spores responded to germinants in a manner similar to *C. sordellii* and *C. difficile*, all spore preparations were tested by germination and growth in litmus milk medium. As expected for *C. perfringens*, all samples showed stormy clot fermentation (Erickson and Deibel, *Appl Environ Microbiol* 1978, 36:567-571). The identities of selected spore samples were further confirmed by repeating 16S rRNA sequencing.

It will be apparent to those skilled in the art that various modifications and variations can be made in the present invention without departing from the scope or spirit of the invention. Other aspects of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for preventing a disease caused by infection by *Clostridium perfringens* in a subject, the method comprising administering to the subject an effective amount of a compound having a structure represented by a formula:

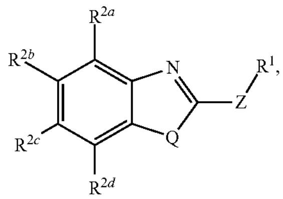

wherein Q is selected from O, S, and $NR^3$:
wherein $R^3$, when present, is selected from hydrogen and C1-C8 alkyl;
wherein Z is selected from O, S, and $NR^4$:
wherein $R^4$, when present, is selected from hydrogen and C1-C8 alkyl;
wherein $R^1$ is selected from hydrogen, C1-C8 alkyl, C1-C8 haloalkyl, $-CR^{5a}R^{5b}(C{=}O)NHN{=}CR^6Ar^1$, $Cy^1$, and $Ar^2$, provided that if Q is $NR^3$ then $R^1$ is not-$CR^{5a}R^{5b}(C{=}O)NHN{=}CR^6Ar^1$:
wherein each of $R^{5a}$ and $R^{5b}$, when present, is independently selected from hydrogen and C1-C4 alkyl;
wherein $R^6$, when present, is selected from hydrogen and C1-C4 alkyl;
wherein $Cy^1$ is selected from C3-C7 cycloalkyl and C2-C7 heterocycloalkyl and substituted with 0, 1, or 2 groups independently selected from halogen, —OH, —CN, $—NO_2$, $—NH_2$, C1-C4 alkyl, C1-C4 alkoxy, C1-C4 haloalkyl, C1-C4 alkylamino, and (C1-C4)(C1-C4) dialkylamino;
wherein $Ar^1$ is selected from aryl and heteroaryl and substituted with 0, 1, or 2 groups independently selected from halogen, —OH, —CN, $—NO_2$, $—NH_2$, C1-C4 alkyl, C1-C4 alkoxy, C1-C4 haloalkyl, C1-C4 alkylamino, and (C1-C4)(C1-C4) dialkylamino;
wherein $Ar^2$ is selected from aryl and heteroaryl and substituted with 0, 1, or 2 groups independently selected from halogen, —OH, —CN, $—NO_2$, $—NH_2$, C1-C4 alkyl, C1-C4 alkoxy, C1-C4 haloalkyl, C1-C4 alkylamino, and (C1-C4)(C1-C4) dialkylamino; and
wherein each of $R^{2a}$, $R^{2b}$, $R^{2c}$, and $R^{2d}$ is hydrogen,
thereby preventing the disease caused by infection by *Clostridium perfringens* in a subject.

2. The method of claim 1, wherein $R^1$ is selected from hydrogen, C1-C8 alkyl, C1-C8 haloalkyl, $Cy^1$, and $Ar^2$.

3. The method of claim 1, wherein $R^1$ is C1-C4 alkyl.

4. The method of claim 1, wherein Z is selected from O and $NR^4$;
wherein $R^1$ is selected from hydrogen, C1-C3 alkyl, and C1-C3 haloalkyl; and
wherein $R^4$, when present, is selected from hydrogen and C1-C3 alkyl.

5. The method of claim 1, wherein the compound has a structure represented by a formula:

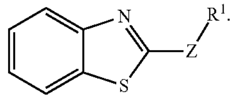

6. The method of claim 1, wherein the compound is selected from:

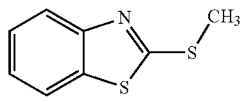

and

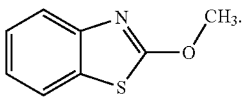

7. The method of claim 1, wherein the disease is necrotizing enteritis.

8. The method of claim 1, wherein the subject is a farm animal.

9. The method of claim 8, wherein the farm animal is selected from a chicken, a turkey, a goose, a duck, a cow, a sheep, a horse, and a pig.

10. A method for inhibiting germination of at least one *Clostridium perfringens* spore, the method comprising contacting the spore with a compound having a structure represented by a formula:

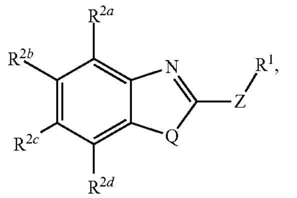

wherein Q is selected from O, S, and $NR^3$;
 wherein $R^3$, when present, is selected from hydrogen and C1-C8 alkyl;
wherein Z is selected from O, S, and $NR^4$;
 wherein $R^4$, when present, is selected from hydrogen and C1-C8 alkyl;
wherein $R^1$ is selected from hydrogen, C1-C8 alkyl, C1-C8 haloalkyl, $—CR^{5a}R^{5b}(C{=}O)NHN{=}CR^6Ar^1$, $Cy^1$, and $Ar^2$, provided that if Q is $NR^3$ then $R^1$ is not-$CR^{5a}R^{5b}(C{=}O)NHN{=}CR^6Ar^1$:
 wherein each of $R^{5a}$ and $R^{5b}$, when present, is independently selected from hydrogen and C1-C4 alkyl;
 wherein $R^6$, when present, is selected from hydrogen and C1-C4 alkyl;
 wherein $Cy^1$ is selected from C3-C7 cycloalkyl and C2-C7 heterocycloalkyl and substituted with 0, 1, or 2 groups independently selected from halogen, —OH, —CN, $—NO_2$, $—NH_2$, C1-C4 alkyl, C1-C4 alkoxy, C1-C4 haloalkyl, C1-C4 alkylamino, and (C1-C4)(C1-C4) dialkylamino;
 wherein $Ar^1$ is selected from aryl and heteroaryl and substituted with 0, 1, or 2 groups independently selected from halogen, —OH, —CN, $—NO_2$, $—NH_2$, C1-C4 alkyl, C1-C4 alkoxy, C1-C4 haloalkyl, C1-C4 alkylamino, and (C1-C4)(C1-C4) dialkylamino;
 wherein $Ar^2$ is selected from aryl and heteroaryl and substituted with 0, 1, or 2 groups independently selected from halogen, —OH, —CN, $—NO_2$, $—NH_2$, C1-C4 alkyl, C1-C4 alkoxy, C1-C4 haloalkyl, C1-C4 alkylamino, and (C1-C4)(C1-C4) dialkylamino; and
wherein each of $R^{2a}$, $R^{2b}$, $R^{2c}$, and $R^{2d}$ is hydrogen,
thereby inhibiting germination of at least one *Clostridium perfringens* spore.

11. The method of claim 10, wherein the spore is in the gut of an animal.

12. The method of claim 10, wherein Z is selected from O and $NR^4$;
wherein $R^1$ is selected from hydrogen, C1-C3 alkyl, and C1-C3 haloalkyl; and
wherein $R^4$, when present, is selected from hydrogen and C1-C3 alkyl.

13. The method of claim 10, wherein the compound is selected from:

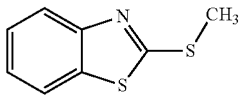

and

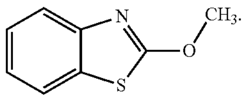

14. A feed composition comprising a feed component and a compound selected from:

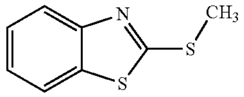

and

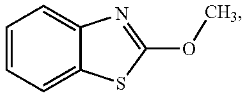

15. The composition of claim 14, wherein the feed component is selected from a vegetable protein, a fat-soluble vitamin, a water soluble vitamin, a trace mineral, and a macro mineral.

16. The composition of claim 14, wherein the composition is a granule.

17. The composition of claim 14, wherein the composition is a pellet.

18. The composition of claim 14, wherein the composition further comprises one or more of an antibiotic, an arsenical, an antioxidant, an antifungal, a probiotic, a flavoring agent, a binder, a pigment, a preservative, an emulsifier, and a sweetener.

19. The composition of claim 14, wherein the compound is:

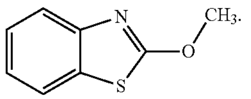 [SMILES: COc1nc2ccccc2s1]

* * * * *